United States Patent
Morton

(10) Patent No.: US 10,591,424 B2
(45) Date of Patent: *Mar. 17, 2020

(54) X-RAY TOMOGRAPHIC INSPECTION SYSTEMS FOR THE IDENTIFICATION OF SPECIFIC TARGET ITEMS

(75) Inventor: Edward James Morton, Guildford, Surrey (GB)

(73) Assignee: Rapiscan Systems, Inc., Torrance, CA (US)

( * ) Notice: Subject to any disclaimer, the term of this patent is extended or adjusted under 35 U.S.C. 154(b) by 2133 days.

This patent is subject to a terminal disclaimer.

(21) Appl. No.: 13/532,862

(22) Filed: Jun. 26, 2012

(65) Prior Publication Data

US 2013/0251098 A1    Sep. 26, 2013

Related U.S. Application Data

(63) Continuation of application No. 12/787,930, filed on May 26, 2010, now Pat. No. 8,223,919, which is a
(Continued)

(30) Foreign Application Priority Data

Apr. 25, 2003  (GB) .................................. 0309371.3
Apr. 25, 2003  (GB) .................................. 0309374.7
(Continued)

(51) Int. Cl.
*G01N 23/046*  (2018.01)
*H01J 35/04*   (2006.01)
*A61B 6/02*    (2006.01)

(52) U.S. Cl.
CPC ............ *G01N 23/046* (2013.01); *H01J 35/04* (2013.01); *H01J 35/045* (2013.01); *A61B 6/027* (2013.01);
(Continued)

(58) Field of Classification Search
CPC .............................. G01N 23/046; A61B 6/032
(Continued)

(56) References Cited

U.S. PATENT DOCUMENTS 2,299,251 A   10/1942  Perbal
2,831,123 A    4/1958  Daly
(Continued)

FOREIGN PATENT DOCUMENTS

AT        392160 B      2/1991
AU     2003254124 A1    2/2004
(Continued)

OTHER PUBLICATIONS

US 5,987,079 A, 11/1999, Scott (withdrawn)
(Continued)

*Primary Examiner* — Courtney D Thomas
(74) *Attorney, Agent, or Firm* — Novel IP

(57) ABSTRACT

The present specification discloses an X-ray scanning system with a non-rotating X-ray scanner that generates scanning data defining a tomographic X-ray image of the object and a processor executing programmatic instructions where the executing processor analyzes the scanning data to extract at least one parameter of the tomographic X-ray image and where the processor is configured to determine if the object comprises a liquid, sharp object, narcotic, currency, nuclear materials, cigarettes or fire-arms.

80 Claims, 12 Drawing Sheets

Related U.S. Application Data continuation-in-part of application No. 12/485,897, filed on Jun. 16, 2009, now abandoned, which is a continuation of application No. 10/554,656, filed as application No. PCT/GB2004/001729 on Apr. 23, 2004, now Pat. No. 7,564,939, said application No. 12/787,930 is a continuation-in-part of application No. 12/371,853, filed on Feb. 16, 2009, now Pat. No. 7,903,789, which is a continuation of application No. 10/554,975, filed as application No. PCT/GB2004/001741 on Apr. 23, 2004, now Pat. No. 7,512,215, said application No. 12/787,930 is a continuation-in-part of application No. 12/651,479, filed on Jan. 3, 2010, now abandoned, which is a continuation of application No. 10/554,654, filed as application No. PCT/GB2004/001731 on Apr. 23, 2004, now Pat. No. 7,664,230, said application No. 12/787,930 is a continuation-in-part of application No. 12/364,067, filed on Feb. 2, 2009, now abandoned, which is a continuation of application No. 12/033,035, filed on Feb. 19, 2008, now Pat. No. 7,505,563, which is a continuation of application No. 10/554,569, filed as application No. PCT/GB2004/001732 on Apr. 23, 2004, now Pat. No. 7,349,525, said application No. 12/787,930 is a continuation-in-part of application No. 12/758,764, filed on Apr. 12, 2010, now Pat. No. 7,929,663, which is a continuation of application No. 12/211,219, filed on Sep. 16, 2008, now Pat. No. 7,724,868, which is a continuation of application No. 10/554,655, filed as application No. PCT/GB2004/001751 on Apr. 23, 2004, now Pat. No. 7,440,543, said application No. 12/787,930 is a continuation-in-part of application No. 12/697,073, filed on Jan. 29, 2010, now Pat. No. 8,085,897, which is a continuation of application No. 10/554,570, filed as application No. PCT/GB2004/001747 on Apr. 23, 2004, now Pat. No. 7,684,538, said application No. 12/787,930 is a continuation-in-part of application No. 12/097,422, filed as application No. PCT/GB2006/004684 on Dec. 15, 2006, now Pat. No. 7,876,879, said application No. 12/787,930 is a continuation-in-part of application No. 12/142,005, filed as application No. PCT/GB2006/004684 on Dec. 15, 2006, now Pat. No. 8,135,110, said application No. 12/787,930 is a continuation-in-part of application No. 12/478,757, filed on Jun. 4, 2009, now Pat. No. 8,094,784, which is a continuation of application No. 12/364,067, filed on Feb. 2, 2009, now abandoned, which is a continuation of application No. 12/033,035, filed on Feb. 19, 2008, now Pat. No. 7,505,563, which is a continuation of application No. 10/554,569, filed as application No. PCT/GB2004/001732 on Apr. 23, 2004, now Pat. No. 7,349,525, said application No. 12/787,930 is a continuation-in-part of application No. 12/712,476, filed on Feb. 25, 2010, now Pat. No. 8,243,876.

(60) Provisional application No. 61/155,572, filed on Feb. 26, 2009, provisional application No. 61/181,068, filed on May 26, 2009.

(30) Foreign Application Priority Data

| Apr. 25, 2003 | (GB) | 0309379.6 |
|---|---|---|
| Apr. 25, 2003 | (GB) | 0309383.8 |
| Apr. 25, 2003 | (GB) | 0309385.3 |
| Apr. 25, 2003 | (GB) | 0309387.9 |
| Dec. 16, 2005 | (GB) | 0525593.0 |
| Jul. 15, 2008 | (GB) | 0812864.7 |
| Feb. 25, 2009 | (GB) | 0903198.0 |

(52) U.S. Cl.
CPC . *G01N 2223/419* (2013.01); *G01N 2223/639* (2013.01); *H01J 2235/068* (2013.01)

(58) Field of Classification Search
USPC .......................................................... 378/57
See application file for complete search history.

(56) References Cited

U.S. PATENT DOCUMENTS

| 2,952,790 | A | 9/1960 | Steen |
|---|---|---|---|
| 2,999,935 | A | 9/1961 | Foster |
| 3,143,651 | A | 8/1964 | Riccardo |
| 3,239,706 | A | 3/1966 | Farrell |
| 3,707,672 | A | 12/1972 | Miller |
| 3,713,156 | A | 1/1973 | Pothier |
| 3,766,387 | A | 10/1973 | Heffan |
| 3,768,645 | A | 10/1973 | Conway |
| 3,780,291 | A | 12/1973 | Stein |
| 3,784,837 | A | 1/1974 | Holmstrom |
| 3,790,785 | A | 2/1974 | Paolini |
| 3,790,799 | A | 2/1974 | Stein |
| 3,848,130 | A | 11/1974 | Macovski |
| 3,854,049 | A | 12/1974 | Mistretta |
| RE28,544 | E | 9/1975 | Stein |
| 3,965,358 | A | 6/1976 | Macovski |
| 3,980,889 | A | 9/1976 | Haas |
| 4,031,401 | A | 6/1977 | Jacob |
| 4,031,545 | A | 6/1977 | Stein |
| 4,047,035 | A | 9/1977 | Dennhoven |
| 4,057,725 | A | 11/1977 | Wagner |
| 4,105,922 | A | 8/1978 | Lambert |
| 4,122,783 | A | 10/1978 | Pretini |
| 4,139,771 | A | 2/1979 | Dennhoven |
| 4,158,770 | A | 6/1979 | Davis, Jr. |
| 4,185,205 | A | 1/1980 | Ballas |
| 4,200,800 | A | 4/1980 | Swift |
| 4,210,811 | A | 7/1980 | Dennhoven |
| 4,216,499 | A | 8/1980 | Dennhoven |
| 4,228,353 | A | 10/1980 | Johnson |
| 4,228,357 | A | 10/1980 | Annis |
| 4,242,583 | A | 12/1980 | Annis |
| 4,245,158 | A | 1/1981 | Burstein |
| 4,259,721 | A | 3/1981 | Kuznia |
| 4,260,898 | A | 4/1981 | Annis |
| 4,266,425 | A | 5/1981 | Allport |
| 4,274,005 | A | 6/1981 | Yamamura |
| 4,297,580 | A | 10/1981 | Juner |
| 4,303,860 | A | 12/1981 | Bjorkholm |
| 4,340,816 | A | 7/1982 | Schott |
| 4,342,914 | A | 8/1982 | Bjorkholm |
| 4,352,021 | A | 9/1982 | Boyd |
| 4,366,382 | A | 12/1982 | Kotowski |
| 4,366,576 | A | 12/1982 | Annis |
| 4,375,695 | A | 3/1983 | Harding |
| 4,384,209 | A | 5/1983 | Wagner |
| 4,389,729 | A | 6/1983 | Stein |
| 4,399,403 | A | 8/1983 | Strandberg, Jr. |
| 4,414,682 | A | 11/1983 | Annis |
| 4,422,177 | A | 12/1983 | Mastronardi |
| 4,430,568 | A | 2/1984 | Yoshida |
| 4,468,802 | A | 8/1984 | Friedel |
| 4,471,343 | A | 9/1984 | Lemelson |
| 4,472,822 | A | 9/1984 | Swift |
| 4,511,799 | A | 4/1985 | Bjorkholm |
| 4,566,113 | A | 1/1986 | Doenges |
| 4,571,491 | A | 2/1986 | Vinegar |
| 4,593,355 | A | 6/1986 | Chase |
| 4,599,740 | A | 7/1986 | Cable |
| 4,622,688 | A | 11/1986 | Diemer |
| 4,641,330 | A | 2/1987 | Herwig |
| 4,672,649 | A | 6/1987 | Rutt |

(56) References Cited

U.S. PATENT DOCUMENTS

| | | |
|---|---|---|
| 4,675,890 A | 6/1987 | Plessis |
| 4,691,332 A | 9/1987 | Burstein |
| 4,736,401 A | 4/1988 | Donges |
| 4,754,469 A | 6/1988 | Harding |
| 4,768,214 A | 8/1988 | Bjorkholm |
| 4,788,704 A | 11/1988 | Donges |
| 4,788,706 A | 11/1988 | Jacobson |
| 4,789,930 A | 12/1988 | Sones |
| 4,799,247 A | 1/1989 | Annis |
| 4,809,312 A | 2/1989 | Annis |
| 4,825,454 A | 4/1989 | Annis |
| RE32,961 E | 6/1989 | Wagner |
| 4,845,769 A | 7/1989 | Burstein |
| 4,852,131 A | 7/1989 | Armistead |
| 4,866,745 A | 9/1989 | Akai |
| 4,868,856 A | 9/1989 | Frith |
| 4,884,289 A | 11/1989 | Glockmann |
| 4,887,604 A | 12/1989 | Shefer |
| 4,893,015 A | 1/1990 | Kubierschky |
| 4,899,283 A | 2/1990 | Annis |
| 4,956,856 A | 9/1990 | Harding |
| 4,958,363 A | 9/1990 | Nelson |
| 4,975,968 A | 12/1990 | Yukl |
| 4,979,202 A | 12/1990 | Siczek |
| 4,987,584 A | 1/1991 | Doenges |
| 4,991,189 A | 2/1991 | Boomgaarden |
| 5,007,072 A | 4/1991 | Jenkins |
| 5,008,911 A | 4/1991 | Harding |
| 5,022,062 A | 6/1991 | Annis |
| 5,033,106 A | 7/1991 | Kita |
| 5,056,124 A | 10/1991 | Kakimoto |
| 5,065,418 A | 11/1991 | Bermbach |
| 5,081,456 A | 1/1992 | Michiguchi |
| 5,091,924 A | 2/1992 | Bermbach |
| 5,098,640 A | 3/1992 | Gozani |
| 5,105,452 A | 4/1992 | McInerney |
| 5,127,030 A | 6/1992 | Annis |
| 5,144,191 A | 9/1992 | Jones |
| 5,155,365 A | 10/1992 | Cann |
| 5,172,401 A | 12/1992 | Asari |
| 5,179,581 A | 1/1993 | Annis |
| 5,181,234 A | 1/1993 | Smith |
| 5,182,764 A | 1/1993 | Peschmann |
| 5,224,144 A | 6/1993 | Annis |
| 5,227,800 A | 7/1993 | Huguenin |
| 5,237,598 A | 8/1993 | Albert |
| 5,247,556 A | 9/1993 | Eckert |
| 5,247,561 A | 9/1993 | Kotowski |
| 5,253,283 A | 10/1993 | Annis |
| 5,259,014 A | 11/1993 | Brettschneider |
| 5,263,075 A | 11/1993 | McGann |
| 5,265,144 A | 11/1993 | Harding |
| 5,272,627 A | 12/1993 | Maschhoff |
| 5,313,511 A | 5/1994 | Annis |
| 5,319,547 A | 6/1994 | Krug |
| 5,339,080 A | 8/1994 | Steinway |
| 5,345,240 A | 9/1994 | Frazier |
| 5,365,567 A | 11/1994 | Ohtsuchi |
| 5,367,552 A | 11/1994 | Peschmann |
| 5,379,334 A | 1/1995 | Zimmer |
| 5,410,156 A | 4/1995 | Miller |
| 5,412,702 A | 5/1995 | Sata |
| 5,420,905 A | 5/1995 | Bertozzi |
| 5,467,377 A | 11/1995 | Dawson |
| 5,481,584 A | 1/1996 | Tang |
| 5,490,196 A | 2/1996 | Rudich |
| 5,490,218 A | 2/1996 | Krug |
| 5,493,596 A | 2/1996 | Annis |
| 5,511,104 A | 4/1996 | Mueller |
| 5,524,133 A | 6/1996 | Neale |
| 5,552,705 A | 9/1996 | Keller |
| 5,557,108 A | 9/1996 | Tumer |
| 5,557,283 A | 9/1996 | Sheen |
| 5,570,403 A | 10/1996 | Yamazaki |
| 5,600,303 A | 2/1997 | Husseiny |
| 5,600,700 A * | 2/1997 | Krug ............ G01N 23/201 376/159 |
| 5,604,778 A | 2/1997 | Polacin |
| 5,606,167 A | 2/1997 | Miller |
| 5,633,906 A | 5/1997 | Hell |
| 5,633,907 A | 5/1997 | Gravelle |
| 5,638,420 A | 6/1997 | Armistead |
| 5,642,393 A | 6/1997 | Krug |
| 5,642,394 A | 6/1997 | Rothschild |
| 5,648,997 A | 7/1997 | Chao |
| 5,651,047 A | 7/1997 | Moorman |
| 5,661,774 A | 8/1997 | Gordon |
| 5,666,393 A | 9/1997 | Annis |
| 5,687,210 A | 11/1997 | Maitrejean |
| 5,689,239 A | 11/1997 | Turner |
| 5,689,541 A | 11/1997 | Schardt |
| 5,692,028 A | 11/1997 | Geus |
| 5,712,926 A | 1/1998 | Eberhard |
| 5,745,543 A | 4/1998 | De Bokx |
| 5,751,837 A | 5/1998 | Watanabe |
| 5,764,683 A | 6/1998 | Swift |
| 5,768,334 A | 6/1998 | Maitrejean |
| 5,787,145 A | 7/1998 | Geus |
| 5,796,802 A | 8/1998 | Gordon |
| 5,805,660 A | 9/1998 | Perion |
| 5,812,630 A | 9/1998 | Blaffert |
| 5,818,897 A | 10/1998 | Gordon |
| 5,838,758 A | 11/1998 | Krug |
| 5,838,759 A | 11/1998 | Armistead |
| 5,841,831 A | 11/1998 | Hell |
| 5,859,891 A | 1/1999 | Hibbard |
| 5,881,122 A | 3/1999 | Crawford |
| 5,887,047 A | 3/1999 | Bailey |
| 5,901,198 A | 5/1999 | Crawford |
| 5,903,623 A | 5/1999 | Swift |
| 5,905,806 A | 5/1999 | Eberhard |
| 5,909,477 A | 6/1999 | Crawford |
| 5,910,973 A | 6/1999 | Grodzins |
| 5,930,326 A | 7/1999 | Rothschild |
| 5,940,468 A | 8/1999 | Huang |
| 5,943,388 A | 8/1999 | Tuemer |
| 5,966,422 A | 10/1999 | Dafni |
| 5,974,111 A | 10/1999 | Krug |
| 5,982,843 A | 11/1999 | Bailey |
| 5,987,097 A | 11/1999 | Salasoo |
| 6,018,562 A | 1/2000 | Willson |
| 6,021,174 A | 2/2000 | Campbell |
| 6,026,135 A | 2/2000 | McFee |
| 6,026,143 A | 2/2000 | Simanovsky |
| 6,026,171 A | 2/2000 | Hiraoglu |
| 6,031,890 A | 2/2000 | Bermbach |
| 6,035,014 A | 3/2000 | Hiraoglu |
| 6,037,597 A | 3/2000 | Karavolos |
| 6,054,712 A | 4/2000 | Komardin |
| 6,058,158 A | 5/2000 | Eiler |
| 6,067,344 A | 5/2000 | Grodzins |
| 6,067,366 A | 5/2000 | Simanovsky |
| 6,075,871 A | 6/2000 | Simanovsky |
| 6,076,400 A | 6/2000 | Bechwati |
| 6,078,642 A | 6/2000 | Simanovsky |
| 6,081,580 A | 6/2000 | Grodzins |
| 6,088,423 A | 7/2000 | Krug |
| 6,091,795 A | 7/2000 | Schafer |
| 6,094,472 A | 7/2000 | Smith |
| 6,108,396 A | 8/2000 | Bechwati |
| 6,111,974 A | 8/2000 | Hiraoglu |
| 6,118,850 A | 9/2000 | Mayo |
| 6,118,852 A | 9/2000 | Rogers |
| 6,122,343 A | 9/2000 | Pidcock |
| 6,125,167 A | 9/2000 | Morgan |
| 6,128,365 A | 10/2000 | Bechwati |
| 6,149,592 A | 11/2000 | Yanof |
| 6,151,381 A | 11/2000 | Grodzins |
| 6,163,591 A | 12/2000 | Benjamin |
| 6,181,765 B1 | 1/2001 | Sribar |
| 6,183,139 B1 | 2/2001 | Solomon |
| 6,184,841 B1 | 2/2001 | Shober |
| 6,185,272 B1 | 2/2001 | Hiraoglu |
| 6,188,743 B1 | 2/2001 | Tybinkowski |

(56) References Cited

U.S. PATENT DOCUMENTS

| | | |
|---|---|---|
| 6,188,745 B1 | 2/2001 | Gordon |
| 6,188,747 B1 | 2/2001 | Geus |
| 6,192,101 B1 | 2/2001 | Grodzins |
| 6,192,104 B1 | 2/2001 | Adams |
| 6,195,413 B1 | 2/2001 | Geus |
| 6,195,444 B1 | 2/2001 | Simanovsky |
| 6,198,795 B1 | 3/2001 | Naumann |
| 6,216,540 B1 | 4/2001 | Nelson |
| 6,218,943 B1 | 4/2001 | Ellenbogen |
| 6,236,709 B1 | 5/2001 | Perry |
| 6,249,567 B1 | 6/2001 | Rothschild |
| 6,252,929 B1 | 6/2001 | Swift |
| 6,252,932 B1 | 6/2001 | Arakawa |
| 6,256,369 B1 | 7/2001 | Lai |
| 6,256,404 B1 | 7/2001 | Gordon |
| 6,269,142 B1 | 7/2001 | Smith |
| 6,272,230 B1 | 8/2001 | Hiraoglu |
| 6,278,115 B1 | 8/2001 | Annis |
| 6,282,260 B1 | 8/2001 | Grodzins |
| 6,288,676 B1 | 9/2001 | Maloney |
| 6,292,533 B1 | 9/2001 | Swift |
| 6,301,326 B2 | 10/2001 | Bjorkholm |
| 6,304,629 B1 | 10/2001 | Conway |
| 6,317,509 B1 | 11/2001 | Simanovsky |
| 6,320,933 B1 | 11/2001 | Grodzins |
| 6,324,249 B1 | 11/2001 | Fazzio |
| 6,342,696 B1 | 1/2002 | Chadwick |
| 6,345,113 B1 | 2/2002 | Crawford |
| 6,347,132 B1 | 2/2002 | Annis |
| 6,356,620 B1 | 3/2002 | Rothschild |
| 6,359,582 B1 | 3/2002 | MacAleese |
| 6,385,292 B1 | 5/2002 | Dunham |
| 6,417,797 B1 | 7/2002 | Cousins |
| 6,418,189 B1 | 7/2002 | Schafer |
| 6,421,420 B1 | 7/2002 | Grodzins |
| 6,424,695 B1 | 7/2002 | Grodzins |
| 6,429,578 B1 | 8/2002 | Danielsson |
| 6,430,255 B2 | 8/2002 | Fenkart |
| 6,434,219 B1 | 8/2002 | Rothschild |
| 6,435,715 B1 | 8/2002 | Betz |
| 6,442,233 B1 | 8/2002 | Grodzins |
| 6,445,765 B1 | 9/2002 | Frank |
| 6,453,003 B1 | 9/2002 | Springer |
| 6,453,007 B2 | 9/2002 | Adams |
| 6,456,093 B1 | 9/2002 | Merkel |
| 6,456,684 B1 | 9/2002 | Mun |
| 6,459,755 B1 | 10/2002 | Li |
| 6,459,761 B1 | 10/2002 | Grodzins |
| 6,459,764 B1 | 10/2002 | Chalmers |
| 6,469,624 B1 | 10/2002 | Whan |
| 6,473,487 B1 | 10/2002 | Le |
| RE37,899 E | 11/2002 | Grodzins |
| 6,480,141 B1 | 11/2002 | Toth |
| 6,483,894 B2 | 11/2002 | Hartick |
| 6,501,414 B2 | 12/2002 | Arndt |
| 6,507,025 B1 | 1/2003 | Verbinski |
| 6,532,276 B1 | 3/2003 | Hartick |
| 6,542,574 B2 | 4/2003 | Grodzins |
| 6,542,578 B2 | 4/2003 | Ries |
| 6,542,580 B1 | 4/2003 | Carver |
| 6,546,072 B1 | 4/2003 | Chalmers |
| 6,552,346 B2 | 4/2003 | Verbinski |
| 6,556,653 B2 | 4/2003 | Hussein |
| 6,563,903 B2 | 5/2003 | Kang |
| 6,563,906 B2 | 5/2003 | Hussein |
| 6,580,778 B2 | 6/2003 | Meder |
| 6,584,170 B2 | 6/2003 | Aust |
| 6,590,956 B2 | 7/2003 | Fenkart |
| 6,597,760 B2 | 7/2003 | Beneke |
| 6,606,516 B2 | 8/2003 | Levine |
| 6,618,466 B1 | 9/2003 | Ning |
| 6,621,888 B2 | 9/2003 | Grodzins |
| 6,628,745 B1 | 9/2003 | Annis |
| 6,636,581 B2 | 10/2003 | Sorenson |
| 6,642,513 B1 | 11/2003 | Jenkins |
| 6,647,091 B2 | 11/2003 | Fenkart |
| 6,647,094 B2 | 11/2003 | Harding |
| 6,647,095 B2 | 11/2003 | Hsieh |
| 6,650,276 B2 | 11/2003 | Lawless |
| 6,653,588 B1 | 11/2003 | Gillard-Hickman |
| 6,654,440 B1 | 11/2003 | Hsieh |
| 6,658,087 B2 | 12/2003 | Chalmers |
| 6,661,866 B1 | 12/2003 | Limkeman |
| 6,663,280 B2 | 12/2003 | Doenges |
| 6,665,373 B1 | 12/2003 | Kotowski |
| 6,665,433 B2 | 12/2003 | Roder |
| 6,687,333 B2 | 2/2004 | Carroll |
| 6,690,766 B2 | 2/2004 | Kresse |
| 6,707,879 B2 | 3/2004 | McClelland |
| 6,715,533 B2 | 4/2004 | Kresse |
| 6,721,387 B1 | 4/2004 | Naidu |
| 6,735,271 B1 | 5/2004 | Rand |
| 6,737,652 B2 | 5/2004 | Lanza |
| 6,748,043 B1 | 6/2004 | Dobbs |
| 6,754,298 B2 | 6/2004 | Fessler |
| 6,760,407 B2 | 7/2004 | Price |
| 6,763,635 B1 | 7/2004 | Lowman |
| 6,768,317 B2 | 7/2004 | Moeller |
| 6,770,884 B2 | 8/2004 | Bryman |
| 6,775,348 B2 | 8/2004 | Hoffman |
| 6,785,357 B2 | 8/2004 | Bernardi |
| 6,785,359 B2 | 8/2004 | Lemaitre |
| 6,788,761 B2 | 9/2004 | Bijjani |
| 6,798,863 B2 | 9/2004 | Sato |
| 6,807,248 B2 | 10/2004 | Mihara |
| 6,812,426 B1 | 11/2004 | Kotowski |
| 6,813,374 B1 | 11/2004 | Karimi |
| 6,815,670 B2 | 11/2004 | Jenkins |
| 6,816,571 B2 | 11/2004 | Bijjani |
| 6,827,265 B2 | 12/2004 | Knowles |
| 6,830,185 B2 | 12/2004 | Tsikos |
| 6,831,590 B1 | 12/2004 | Steinway |
| 6,837,422 B1 | 1/2005 | Meder |
| 6,837,432 B2 | 1/2005 | Tsikos |
| 6,839,403 B1 | 1/2005 | Kotowski |
| 6,840,122 B1 | 1/2005 | Jenkins |
| 6,843,599 B2 | 1/2005 | Le |
| 6,856,271 B1 | 2/2005 | Hausner |
| 6,856,667 B2 | 2/2005 | Ellenbogen |
| 6,859,514 B2 | 2/2005 | Hoffman |
| 6,876,322 B2 | 4/2005 | Keller |
| 6,891,381 B2 | 5/2005 | Bailey |
| 6,894,636 B2 | 5/2005 | Anderton |
| 6,901,135 B2 | 5/2005 | Fox |
| 6,906,329 B2 | 6/2005 | Bryman |
| 6,907,101 B2 | 6/2005 | Hoffman |
| 6,920,196 B2 | 7/2005 | Ueno |
| 6,920,197 B2 | 7/2005 | Kang |
| 6,922,455 B2 | 7/2005 | Jurczyk |
| 6,922,460 B2 | 7/2005 | Skatter |
| 6,922,461 B2 | 7/2005 | Kang |
| 6,928,141 B2 | 8/2005 | Carver |
| 6,933,504 B2 | 8/2005 | Hoffman |
| 6,934,354 B2 | 8/2005 | Hoffman |
| 6,940,071 B2 | 9/2005 | Ramsden |
| 6,944,264 B2 | 9/2005 | Bijjani |
| 6,947,517 B2 | 9/2005 | Hoffman |
| 6,950,492 B2 | 9/2005 | Besson |
| 6,950,493 B2 | 9/2005 | Besson |
| 6,952,163 B2 | 10/2005 | Huey |
| 6,953,935 B1 | 10/2005 | Hoffman |
| 6,957,913 B2 | 10/2005 | Renkart |
| 6,962,289 B2 | 11/2005 | Vatan |
| 6,968,030 B2 | 11/2005 | Hoffman |
| 6,968,034 B2 | 11/2005 | Ellenbogen |
| 6,971,577 B2 | 12/2005 | Tsikos |
| 6,973,158 B2 | 12/2005 | Besson |
| 6,975,698 B2 | 12/2005 | Katcha |
| 6,975,703 B2 | 12/2005 | Wilson |
| 6,978,936 B2 | 12/2005 | Tsikos |
| 6,980,627 B2 | 12/2005 | Qiu |
| 6,990,171 B2 | 1/2006 | Toth |
| 6,990,172 B2 | 1/2006 | Toth |
| 6,991,371 B2 | 1/2006 | Georgeson |

(56) References Cited

U.S. PATENT DOCUMENTS

| | | |
|---|---|---|
| 6,993,115 B2 | 1/2006 | McGuire |
| 6,996,209 B2 | 2/2006 | Marek |
| 7,010,083 B2 | 3/2006 | Hoffman |
| 7,010,094 B2 | 3/2006 | Grodzins |
| 7,012,256 B1 | 3/2006 | Roos |
| 7,012,989 B2 | 3/2006 | Holland |
| 7,016,459 B2 | 3/2006 | Ellenbogen |
| 7,020,232 B2 | 3/2006 | Rand |
| 7,020,241 B2 | 3/2006 | Beneke |
| 7,020,242 B2 | 3/2006 | Ellenbogen |
| 7,023,950 B1 | 4/2006 | Annis |
| 7,023,956 B2 | 4/2006 | Heaton |
| 7,023,957 B2 | 4/2006 | Bijjani |
| 7,027,553 B2 | 4/2006 | Dunham |
| 7,027,554 B2 | 4/2006 | Gaultier |
| 7,031,430 B2 | 4/2006 | Kaucic, Jr. |
| 7,031,434 B1 | 4/2006 | Saunders |
| 7,034,313 B2 | 4/2006 | Hoffman |
| 7,039,154 B1 | 5/2006 | Ellenbogen |
| 7,039,159 B2 | 5/2006 | Muenchau |
| 7,045,787 B1 | 5/2006 | Verbinski |
| 7,046,756 B2 | 5/2006 | Hoffman |
| 7,046,761 B2 | 5/2006 | Ellenbogen |
| 7,050,529 B2 | 5/2006 | Hoffman |
| 7,050,536 B1 | 5/2006 | Fenkart |
| 7,050,540 B2 | 5/2006 | Wilkins |
| 7,054,408 B2 | 5/2006 | Jiang |
| 7,062,009 B2 | 6/2006 | Karimi |
| 7,062,011 B1 | 6/2006 | Tybinkowski |
| 7,062,074 B1 | 6/2006 | Beneke |
| 7,064,334 B2 | 6/2006 | Hoffman |
| 7,065,175 B2 | 6/2006 | Green |
| 7,065,179 B2 | 6/2006 | Block |
| 7,068,749 B2 | 6/2006 | Kollegal |
| 7,068,750 B2 | 6/2006 | Toth |
| 7,068,751 B2 | 6/2006 | Toth |
| 7,072,434 B1 | 7/2006 | Tybinkowski |
| 7,076,029 B2 | 7/2006 | Toth |
| 7,078,699 B2 | 7/2006 | Seppi |
| 7,081,628 B2 | 7/2006 | Granfors et al. |
| 7,084,404 B2 | 8/2006 | Hoffman |
| 7,087,902 B2 | 8/2006 | Wang |
| 7,088,799 B2 | 8/2006 | Hoffman |
| 7,090,133 B2 | 8/2006 | Zhu |
| 7,092,481 B2 | 8/2006 | Hoffman |
| 7,092,485 B2 | 8/2006 | Kravis |
| 7,099,434 B2 | 8/2006 | Adams |
| 7,103,137 B2 | 9/2006 | Seppi |
| 7,110,488 B2 | 9/2006 | Katcha |
| 7,110,493 B1 | 9/2006 | Kotowski |
| 7,112,797 B2 | 9/2006 | Hoge |
| 7,116,749 B2 | 10/2006 | Besson |
| 7,116,751 B2 | 10/2006 | Ellenbogen |
| 7,119,553 B2 | 10/2006 | Yang |
| 7,120,222 B2 | 10/2006 | Hoffman |
| 7,123,681 B2 | 10/2006 | Ellenbogen |
| 7,127,027 B2 | 10/2006 | Hoffman |
| 7,130,374 B1 | 10/2006 | Jacobs |
| RE39,396 E | 11/2006 | Swift Roderick |
| 7,133,491 B2 | 11/2006 | Bernardi |
| 7,136,450 B2 | 11/2006 | Ying |
| 7,136,451 B2 | 11/2006 | Naidu |
| 7,139,367 B1 | 11/2006 | Le |
| 7,139,406 B2 | 11/2006 | McClelland |
| 7,142,629 B2 | 11/2006 | Edic |
| 7,149,278 B2 | 12/2006 | Arenson |
| 7,149,339 B2 | 12/2006 | Veneruso |
| 7,155,812 B1 | 1/2007 | Peterson |
| 7,158,611 B2 | 1/2007 | Heismann |
| 7,164,747 B2 | 1/2007 | Ellenbogen |
| 7,164,750 B2 | 1/2007 | Nabors |
| 7,166,458 B2 | 1/2007 | Ballerstadt |
| 7,167,539 B1 | 1/2007 | Hoffman |
| 7,173,998 B2 | 2/2007 | Hoffman |
| 7,177,387 B2 | 2/2007 | Yasunaga |
| 7,177,391 B2 | 2/2007 | Chapin |
| 7,183,906 B2 | 2/2007 | Zanovitch |
| 7,187,756 B2 | 3/2007 | Gohno |
| 7,190,757 B2 | 3/2007 | Ying |
| 7,192,031 B2 | 3/2007 | Dunham |
| 7,197,113 B1 | 3/2007 | Katcha |
| 7,197,116 B2 | 3/2007 | Dunham |
| 7,197,172 B1 | 3/2007 | Naidu |
| 7,203,269 B2 | 4/2007 | Huber |
| 7,203,271 B2 | 4/2007 | Benz |
| 7,203,629 B2 | 4/2007 | Oezis |
| 7,206,379 B2 | 4/2007 | Lemaitre |
| 7,207,713 B2 | 4/2007 | Lowman |
| 7,215,731 B1 | 5/2007 | Basu |
| 7,215,738 B2 | 5/2007 | Muenchau |
| 7,218,700 B2 | 5/2007 | Huber |
| 7,218,704 B1 | 5/2007 | Adams |
| 7,224,763 B2 | 5/2007 | Naidu |
| 7,224,765 B2 | 5/2007 | Ellenbogen |
| 7,224,766 B2 | 5/2007 | Jiang |
| 7,224,769 B2 | 5/2007 | Turner |
| 7,233,640 B2 | 6/2007 | Ikhlef |
| 7,233,644 B1 | 6/2007 | Bendahan |
| 7,236,564 B2 | 6/2007 | Hopkins |
| 7,238,945 B2 | 7/2007 | Hoffman |
| 7,247,856 B2 | 7/2007 | Hoge |
| 7,251,310 B2 | 7/2007 | Smith |
| 7,253,727 B2 | 8/2007 | Jenkins |
| 7,260,170 B2 | 8/2007 | Arenson |
| 7,260,171 B1 | 8/2007 | Arenson |
| 7,260,172 B2 | 8/2007 | Arenson |
| 7,260,173 B2 | 8/2007 | Wakayama |
| 7,260,174 B2 | 8/2007 | Hoffman |
| 7,260,182 B2 | 8/2007 | Toth |
| 7,263,160 B2 | 8/2007 | Schlomka |
| 7,266,180 B1 | 9/2007 | Saunders |
| 7,272,429 B2 | 9/2007 | Walker |
| 7,274,767 B2 | 9/2007 | Clayton |
| 7,277,577 B2 | 10/2007 | Ying |
| 7,279,120 B2 | 10/2007 | Cheng |
| 7,280,631 B2 | 10/2007 | De Man |
| 7,282,727 B2 | 10/2007 | Retsky |
| 7,283,604 B2 | 10/2007 | De Man |
| 7,283,609 B2 | 10/2007 | Possin |
| 7,295,019 B2 | 11/2007 | Yang |
| 7,295,651 B2 | 11/2007 | Delgado |
| 7,298,812 B2 | 11/2007 | Tkaczyk |
| 7,302,083 B2 | 11/2007 | Larson |
| 7,308,073 B2 | 12/2007 | Tkaczyk |
| 7,308,074 B2 | 12/2007 | Jiang |
| 7,308,077 B2 | 12/2007 | Bijjani |
| 7,317,195 B2 | 1/2008 | Eikman |
| 7,317,390 B2 | 1/2008 | Huey |
| 7,319,737 B2 | 1/2008 | Singh |
| 7,322,745 B2 | 1/2008 | Agrawal |
| 7,324,625 B2 | 1/2008 | Eilbert |
| 7,327,853 B2 | 2/2008 | Ying |
| 7,330,527 B2 | 2/2008 | Hoffman |
| 7,330,535 B2 | 2/2008 | Arenson |
| 7,333,587 B2 | 2/2008 | De Man |
| 7,333,588 B2 | 2/2008 | Mistretta |
| 7,333,589 B2 | 2/2008 | Ellenbogen |
| 7,335,887 B1 | 2/2008 | Verbinski |
| 7,336,769 B2 | 2/2008 | Arenson |
| 7,340,525 B1 | 3/2008 | Bhatia |
| 7,349,525 B2 | 3/2008 | Morton |
| 7,366,280 B2 | 4/2008 | Lounsberry |
| 7,366,282 B2 | 4/2008 | Peschmann |
| 7,369,640 B2 | 5/2008 | Seppi |
| 7,369,643 B2 | 5/2008 | Kotowski |
| 7,372,934 B2 | 5/2008 | De Man |
| 7,400,701 B1 | 7/2008 | Cason |
| 7,417,440 B2 | 8/2008 | Peschmann |
| 7,440,543 B2 | 10/2008 | Morton |
| 7,483,510 B2 | 1/2009 | Carver |
| 7,486,768 B2 | 2/2009 | Allman |
| 7,486,769 B2 | 2/2009 | Brondo, Jr. |
| 7,492,855 B2 | 2/2009 | Hopkins |
| 7,505,563 B2 | 3/2009 | Morton |

(56) References Cited

U.S. PATENT DOCUMENTS

| | | |
|---|---|---|
| 7,512,215 B2 | 3/2009 | Morton |
| 7,551,714 B2 | 6/2009 | Rothschild |
| 7,551,718 B2 | 6/2009 | Rothschild |
| 7,555,099 B2 | 6/2009 | Rothschild |
| 7,564,939 B2 | 7/2009 | Morton |
| 7,579,845 B2 | 8/2009 | Peschmann |
| 7,590,215 B2 | 9/2009 | Schlomka |
| 7,593,506 B2 | 9/2009 | Cason |
| 7,596,275 B1 | 9/2009 | Richardson |
| 7,643,866 B2 | 1/2010 | Heismann |
| 7,649,981 B2 | 1/2010 | Seppi |
| 7,664,230 B2 | 2/2010 | Morton |
| 7,684,538 B2 | 3/2010 | Morton |
| 7,724,868 B2 | 5/2010 | Morton |
| 7,734,066 B2 | 6/2010 | Delia |
| 7,778,382 B2 | 8/2010 | Hoffman |
| 7,864,920 B2 | 1/2011 | Rothschild |
| 7,876,879 B2 | 1/2011 | Morton |
| 7,903,789 B2 | 3/2011 | Morton |
| 7,924,979 B2 | 4/2011 | Rothschild |
| 7,929,663 B2 | 4/2011 | Morton |
| 7,949,101 B2 | 5/2011 | Morton |
| 7,995,707 B2 | 8/2011 | Rothschild |
| 8,085,897 B2 | 12/2011 | Morton |
| 8,094,784 B2 | 1/2012 | Morton |
| 8,135,110 B2 | 3/2012 | Morton |
| 8,138,770 B2 | 3/2012 | Peschmann |
| 8,204,173 B2 | 6/2012 | Betcke |
| 8,223,919 B2* | 7/2012 | Morton ............ G01N 23/046 378/57 |
| 8,243,876 B2 | 8/2012 | Morton |
| 8,331,535 B2 | 12/2012 | Morton |
| 8,451,974 B2 | 5/2013 | Morton |
| 8,552,722 B2 | 10/2013 | Lionheart |
| 8,559,592 B2 | 10/2013 | Betcke |
| 8,625,735 B2 | 1/2014 | Morton |
| 8,804,899 B2 | 8/2014 | Morton |
| 8,824,637 B2 | 9/2014 | Morton |
| 8,837,669 B2 | 9/2014 | Morton |
| 8,842,808 B2 | 9/2014 | Rothschild |
| 8,885,794 B2 | 11/2014 | Morton |
| 8,958,526 B2 | 2/2015 | Morton |
| 8,971,484 B2 | 3/2015 | Beckmann |
| 9,001,973 B2 | 4/2015 | Morton |
| 9,020,095 B2 | 4/2015 | Morton |
| 9,046,465 B2 | 6/2015 | Thompson |
| 9,048,061 B2 | 6/2015 | Morton |
| 9,086,497 B2 | 7/2015 | Bendahan |
| 9,093,245 B2 | 7/2015 | Morton |
| 9,113,839 B2 | 8/2015 | Morton |
| 9,158,030 B2 | 10/2015 | Morton |
| 9,183,647 B2 | 11/2015 | Morton |
| 9,208,988 B2 | 12/2015 | Morton |
| 9,263,225 B2 | 2/2016 | Morton |
| 9,420,677 B2 | 8/2016 | Morton |
| 9,442,082 B2 | 9/2016 | Morton |
| 9,442,213 B2 | 9/2016 | Bendahan |
| 9,562,866 B2 | 2/2017 | Morton |
| 9,576,766 B2 | 2/2017 | Morton |
| 9,606,259 B2 | 3/2017 | Morton |
| 9,618,648 B2 | 4/2017 | Morton |
| 9,638,646 B2 | 5/2017 | Morton |
| 9,675,306 B2 | 6/2017 | Morton |
| 9,714,920 B2 | 7/2017 | Lionheart |
| 9,726,619 B2 | 8/2017 | Thompson |
| 9,747,705 B2 | 8/2017 | Morton |
| 10,107,783 B2 | 10/2018 | Lionheart |
| 10,175,381 B2 | 1/2019 | Morton |
| 10,295,483 B2 | 5/2019 | Morton |
| 2001/0022346 A1 | 9/2001 | Katagami |
| 2001/0022830 A1 | 9/2001 | Sommer |
| 2001/0033635 A1 | 10/2001 | Kuwabara |
| 2001/0050972 A1 | 12/2001 | Yamada |
| 2002/0008655 A1 | 1/2002 | Haj-Yousef |
| 2002/0031202 A1 | 3/2002 | Callerame |
| 2002/0085674 A1 | 7/2002 | Price |
| 2002/0094064 A1 | 7/2002 | Zhou |
| 2002/0094117 A1 | 7/2002 | Funahashi |
| 2002/0097836 A1 | 7/2002 | Grodzins |
| 2002/0101958 A1 | 8/2002 | Bertsche |
| 2002/0176531 A1 | 11/2002 | McClelland |
| 2003/0009202 A1 | 1/2003 | Levine |
| 2003/0021377 A1 | 1/2003 | Turner |
| 2003/0023592 A1 | 1/2003 | Modica |
| 2003/0031352 A1 | 2/2003 | Nelson |
| 2003/0048868 A1 | 3/2003 | Bailey |
| 2003/0053597 A1 | 3/2003 | Flohr |
| 2003/0076921 A1 | 4/2003 | Mihara |
| 2003/0076924 A1 | 4/2003 | Mario |
| 2003/0085163 A1 | 5/2003 | Chan |
| 2003/0108155 A1 | 6/2003 | Wilkins |
| 2003/0179126 A1 | 9/2003 | Jablonski |
| 2003/0190011 A1 | 10/2003 | Beneke |
| 2003/0216644 A1 | 11/2003 | Hall |
| 2004/0016271 A1 | 1/2004 | Shah |
| 2004/0017224 A1 | 1/2004 | Tumer |
| 2004/0017887 A1 | 1/2004 | Le |
| 2004/0017888 A1 | 1/2004 | Seppi |
| 2004/0077943 A1 | 4/2004 | Meaney |
| 2004/0081270 A1 | 4/2004 | Heuscher |
| 2004/0094707 A1 | 5/2004 | Jenkins |
| 2004/0096030 A1 | 5/2004 | Banchieri |
| 2004/0101098 A1 | 5/2004 | Bijjani |
| 2004/0109532 A1 | 6/2004 | Ford |
| 2004/0120454 A1 | 6/2004 | Ellenbogen |
| 2004/0141584 A1 | 7/2004 | Bernardi |
| 2004/0213378 A1 | 10/2004 | Zhou |
| 2004/0213379 A1 | 10/2004 | Bittl |
| 2004/0223585 A1 | 11/2004 | Heismann |
| 2004/0232054 A1 | 11/2004 | Brown |
| 2004/0234023 A1 | 11/2004 | Kollegal |
| 2004/0245449 A1 | 12/2004 | Nakashige |
| 2004/0252807 A1 | 12/2004 | Skatter |
| 2004/0258198 A1 | 12/2004 | Carver |
| 2004/0258305 A1 | 12/2004 | Burnham |
| 2005/0008073 A1 | 1/2005 | Techmer |
| 2005/0031075 A1 | 2/2005 | Hopkins |
| 2005/0053189 A1 | 3/2005 | Gohno |
| 2005/0057354 A1 | 3/2005 | Jenkins |
| 2005/0058242 A1 | 3/2005 | Peschmann |
| 2005/0084069 A1 | 4/2005 | Du |
| 2005/0084073 A1 | 4/2005 | Seppi |
| 2005/0089140 A1 | 4/2005 | Mario |
| 2005/0105665 A1 | 5/2005 | Grodzins |
| 2005/0105682 A1 | 5/2005 | Heumann |
| 2005/0111610 A1 | 5/2005 | De Man |
| 2005/0111619 A1 | 5/2005 | Bijjani |
| 2005/0117683 A1 | 6/2005 | Mishin |
| 2005/0140603 A1 | 6/2005 | Kim |
| 2005/0157842 A1 | 7/2005 | Agrawal |
| 2005/0157925 A1 | 7/2005 | Lorenz |
| 2005/0169422 A1 | 8/2005 | Ellenbogen |
| 2005/0169423 A1 | 8/2005 | Ellenbogen |
| 2005/0175151 A1 | 8/2005 | Dunham |
| 2005/0180542 A1 | 8/2005 | Leue |
| 2005/0190882 A1 | 9/2005 | McGuire |
| 2005/0226364 A1 | 10/2005 | Bernard De Man |
| 2005/0238232 A1 | 10/2005 | Ying |
| 2005/0249416 A1 | 11/2005 | Leue |
| 2005/0281390 A1 | 12/2005 | Johnson |
| 2006/0002585 A1 | 1/2006 | Larson |
| 2006/0008047 A1 | 1/2006 | Zhou |
| 2006/0018428 A1 | 1/2006 | Li |
| 2006/0056584 A1 | 3/2006 | Allman |
| 2006/0098773 A1 | 5/2006 | Peschmann |
| 2006/0109949 A1 | 5/2006 | Tkaczyk |
| 2006/0113163 A1 | 6/2006 | Hu |
| 2006/0133571 A1 | 6/2006 | Winsor |
| 2006/0134000 A1 | 6/2006 | Heismann |
| 2006/0140341 A1 | 6/2006 | Carver |
| 2006/0203961 A1 | 9/2006 | Morton |
| 2006/0233295 A1 | 10/2006 | Edic |
| 2006/0256924 A1 | 11/2006 | Morton |
| 2006/0273259 A1 | 12/2006 | Li |

(56) References Cited

U.S. PATENT DOCUMENTS

| | | |
|---|---|---|
| 2006/0280286 A1 | 12/2006 | Kaval |
| 2007/0003003 A1 | 1/2007 | Seppi |
| 2007/0025512 A1 | 2/2007 | Gertsenshteyn |
| 2007/0053495 A1 | 3/2007 | Morton |
| 2007/0096030 A1 | 5/2007 | Li |
| 2007/0110215 A1 | 5/2007 | Hu |
| 2007/0122003 A1 | 5/2007 | Dobkin |
| 2007/0133740 A1 | 6/2007 | Kang |
| 2007/0172024 A1 | 7/2007 | Morton |
| 2007/0189597 A1 | 8/2007 | Limer |
| 2007/0242802 A1 | 10/2007 | Dafni |
| 2007/0263767 A1 | 11/2007 | Brondo, Jr. |
| 2007/0269005 A1 | 11/2007 | Chalmers |
| 2008/0144774 A1 | 6/2008 | Mortor |
| 2008/0267355 A1 | 10/2008 | Morton |
| 2008/0304622 A1 | 12/2008 | Morton |
| 2009/0010386 A1 | 1/2009 | Peschmann |
| 2009/0034792 A1 | 2/2009 | Kennison |
| 2009/0041186 A1 | 2/2009 | Gray |
| 2009/0161816 A1 | 6/2009 | De Man |
| 2009/0213989 A1 | 8/2009 | Harding |
| 2009/0274277 A1 | 11/2009 | Morton |
| 2009/0316855 A1 | 12/2009 | Morton |
| 2010/0020934 A1 | 1/2010 | Morton |
| 2010/0172476 A1 | 7/2010 | Morton |
| 2010/0284509 A1 | 11/2010 | Oreper |
| 2012/0219116 A1 | 8/2012 | Thompson |
| 2013/0251098 A1 | 9/2013 | Morton |
| 2013/0264483 A1 | 10/2013 | Abenaim |
| 2014/0023181 A1 | 1/2014 | Noshi |
| 2014/0211916 A1 | 7/2014 | Morton |
| 2014/0294147 A1 | 10/2014 | Chen |
| 2014/0342631 A1 | 11/2014 | Morton |
| 2015/0357148 A1 | 12/2015 | Morton |
| 2016/0343533 A1 | 11/2016 | Morton |
| 2017/0161922 A1 | 6/2017 | Morton |
| 2018/0038988 A1 | 2/2018 | Morton |
| 2018/0128754 A1 | 5/2018 | Thompson |
| 2019/0178821 A1 | 6/2019 | Morton |

FOREIGN PATENT DOCUMENTS

| | | |
|---|---|---|
| CA | 2365045 | 6/2003 |
| CN | 85107860 A | 10/1986 |
| CN | 1050769 | 4/1991 |
| CN | 1130498 A | 9/1996 |
| CN | 1309768 | 8/2001 |
| CN | 1550215 A | 12/2004 |
| CN | 1626039 A | 6/2005 |
| CN | 1708256 A | 12/2005 |
| CN | 1745296 A | 3/2006 |
| CN | 1780585 A | 5/2006 |
| CN | 1795527 A | 6/2006 |
| CN | 100371689 C | 7/2006 |
| CN | 1820705 A | 8/2006 |
| CN | 1937961 A | 3/2007 |
| CN | 101189534 A | 5/2008 |
| DE | 2729353 A1 | 1/1979 |
| DE | 4410757 A1 | 1/1995 |
| DE | 4436688 A1 | 4/1996 |
| DE | 102004056590 A1 | 6/2005 |
| EP | 0198276 A1 | 10/1986 |
| EP | 0424912 A2 | 5/1991 |
| EP | 0432568 | 6/1991 |
| EP | 0531993 A1 | 3/1993 |
| EP | 0564292 | 10/1993 |
| EP | 0584871 A1 | 3/1994 |
| EP | 0795919 A2 | 9/1997 |
| EP | 0873511 A1 | 10/1998 |
| EP | 0924742 A2 | 6/1999 |
| EP | 0930046 A2 | 7/1999 |
| EP | 1277439 A1 | 1/2003 |
| EP | 1298055 A2 | 4/2003 |
| EP | 1371970 A2 | 12/2003 |
| EP | 1374776 A1 | 1/2004 |
| EP | 1540318 A1 | 6/2005 |
| EP | 1558142 A1 | 8/2005 |
| EP | 1618584 A2 | 1/2006 |
| EP | 1689640 A2 | 8/2006 |
| EP | 1739413 | 5/2010 |
| FR | 2328280 A1 | 5/1977 |
| GB | 1497396 A | 1/1978 |
| GB | 1526041 A | 9/1978 |
| GB | 2015245 A | 9/1979 |
| GB | 2089109 A | 6/1982 |
| GB | 2133208 | 7/1984 |
| GB | 2212903 A | 8/1989 |
| GB | 2244900 | 12/1991 |
| GB | 2329817 A | 3/1995 |
| GB | 2285506 A | 7/1995 |
| GB | 2299251 | 9/1996 |
| GB | 2356453 A | 5/2001 |
| GB | 2414072 A | 11/2005 |
| GB | 2416655 A | 2/2006 |
| GB | 2416944 A | 2/2006 |
| GB | 2417821 A | 3/2006 |
| GB | 2418529 A | 3/2006 |
| GB | 2423687 A | 8/2006 |
| GB | 2437777 A | 11/2007 |
| GB | 2471421 A | 12/2010 |
| JE | 62064977 | 3/1987 |
| JP | 50012990 | 2/1975 |
| JP | S5427793 | 3/1979 |
| JP | S5717524 A | 1/1982 |
| JP | 570175247 | 10/1982 |
| JP | S7175247 A | 10/1982 |
| JP | 590016254 A | 1/1984 |
| JP | S5916254 A | 1/1984 |
| JP | 59075549 | 4/1984 |
| JP | 59174744 | 10/1984 |
| JP | 600015546 | 1/1985 |
| JP | S601554 A | 1/1985 |
| JP | 600021440 | 2/1985 |
| JP | S60021440 | 2/1985 |
| JP | 60073442 A | 4/1985 |
| JP | S61028039 | 2/1986 |
| JP | S6104193 | 10/1986 |
| JP | S63150840 | 6/1988 |
| JP | 64034333 A | 2/1989 |
| JP | 05100037 A | 4/1993 |
| JP | 05192327 A | 8/1993 |
| JP | H05060381 | 9/1993 |
| JP | 5325851 | 12/1993 |
| JP | H05325851 | 12/1993 |
| JP | 060038957 | 2/1994 |
| JP | H06133960 | 5/1994 |
| JP | H06169911 | 6/1994 |
| JP | 6296607 | 10/1994 |
| JP | H07012756 | 1/1995 |
| JP | H07057113 | 3/1995 |
| JP | H08178872 | 7/1996 |
| JP | H08299322 | 11/1996 |
| JP | 10005206 A | 1/1998 |
| JP | H10001209 | 1/1998 |
| JP | 10075944 A | 3/1998 |
| JP | 1998075944 A | 3/1998 |
| JP | 10506195 | 6/1998 |
| JP | H10211196 A | 8/1998 |
| JP | 11146871 A | 6/1999 |
| JP | H11230918 | 8/1999 |
| JP | H11230918 A | 8/1999 |
| JP | 11262486 A | 9/1999 |
| JP | 2000107173 A | 4/2000 |
| JP | 200113089 | 1/2001 |
| JP | 2001083171 | 3/2001 |
| JP | 2001176408 A | 6/2001 |
| JP | 2001233440 | 8/2001 |
| JP | 2001351551 | 12/2001 |
| JP | 2002039966 | 2/2002 |
| JP | 2002503816 | 2/2002 |
| JP | 2002162472 | 6/2002 |
| JP | 2002168805 | 6/2002 |
| JP | 2002195961 | 7/2002 |
| JP | 2002257751 | 9/2002 |

(56) References Cited

FOREIGN PATENT DOCUMENTS

| | | |
|---|---|---|
| JP | 2002535625 | 10/2002 |
| JP | 2002320610 A | 11/2002 |
| JP | 2002370814 | 12/2002 |
| JP | 2003126075 A | 5/2003 |
| JP | 2003135442 | 5/2003 |
| JP | 2004000605 A | 1/2004 |
| JP | 2004079128 A | 3/2004 |
| JP | 2004226253 | 8/2004 |
| JP | 2004233206 | 8/2004 |
| JP | 2004347328 | 12/2004 |
| JP | 2005013768 A | 1/2005 |
| JP | 2005110722 | 4/2005 |
| JP | 2005177469 A | 7/2005 |
| JP | 2005534009 | 11/2005 |
| JP | 2005534009 A | 11/2005 |
| JP | 2006502386 | 1/2006 |
| JP | 2006071514 | 3/2006 |
| JP | 2006167463 | 6/2006 |
| JP | 2006518039 | 8/2006 |
| JP | 2006320464 | 11/2006 |
| JP | 2006524809 A | 11/2006 |
| JP | 2007010455 | 1/2007 |
| JP | 2007500357 A | 1/2007 |
| JP | 2007508561 A | 4/2007 |
| JP | 2007533993 A | 11/2007 |
| JP | 2009519457 | 5/2009 |
| NL | 1021026 | 1/2004 |
| NL | 1027596 C2 | 11/2005 |
| WO | 9217771 A1 | 10/1992 |
| WO | 9528715 A2 | 10/1995 |
| WO | 9718462 A1 | 5/1997 |
| WO | 1998002763 A1 | 1/1998 |
| WO | 9941676 | 8/1999 |
| WO | 199950882 | 10/1999 |
| WO | 1999050882 | 10/1999 |
| WO | 9960387 A2 | 11/1999 |
| WO | 0231857 A1 | 4/2002 |
| WO | 200231857 | 4/2002 |
| WO | 2002031857 | 4/2002 |
| WO | 2003029844 | 4/2003 |
| WO | 03042674 | 5/2003 |
| WO | 03051201 A2 | 6/2003 |
| WO | 2003051201 | 6/2003 |
| WO | 2003065772 | 8/2003 |
| WO | 2003088302 | 10/2003 |
| WO | 03105159 | 12/2003 |
| WO | 2004008968 A1 | 1/2004 |
| WO | 2004008970 A1 | 1/2004 |
| WO | 2004010127 A1 | 1/2004 |
| WO | 2004010381 A1 | 1/2004 |
| WO | 2004031755 | 4/2004 |
| WO | 2004031755 A2 | 4/2004 |
| WO | 2004037088 | 5/2004 |
| WO | 2004054329 A2 | 6/2004 |
| WO | 2004072685 | 8/2004 |
| WO | 02004096050 | 11/2004 |
| WO | 2004097344 A2 | 11/2004 |
| WO | 2004097386 A1 | 11/2004 |
| WO | 2004097886 A2 | 11/2004 |
| WO | 2004097888 A2 | 11/2004 |
| WO | 2004097889 A2 | 11/2004 |
| WO | 2004105610 A | 12/2004 |
| WO | 2004111625 | 12/2004 |
| WO | 2005017566 A2 | 2/2005 |
| WO | 2005037074 | 4/2005 |
| WO | 2005050405 A2 | 6/2005 |
| WO | 2005084351 | 9/2005 |
| WO | 2005095931 | 10/2005 |
| WO | 2005102170 | 11/2005 |
| WO | 2006027122 A1 | 3/2006 |
| WO | 2006047718 | 5/2006 |
| WO | 2006074431 A2 | 7/2006 |
| WO | 2006137919 | 12/2006 |
| WO | 2006135586 | 2/2007 |
| WO | 2007051418 | 5/2007 |
| WO | 2007068933 | 6/2007 |
| WO | 2007068933 A1 | 6/2007 |
| WO | 2008024825 A2 | 2/2008 |
| WO | 20012115629 A1 | 8/2012 |

OTHER PUBLICATIONS

Development of ultra-fast X-ray computed tomography scanner system, INS 98-43 6068772 A9823-8760J-016 (PHA); B9812-7510B-113 (EEA) NDN-174-0606-8771-7, Hori, K.; Fujimoto, T.; Kawanishi, K., Editor—Nalcioglu, O., Abbreviated Journal Title—1997 IEEE Nuclear Science Symposium, Conference Record (Cat. No. 97CH36135), Part No. vol. 2, 1997, pp. 1003-1008 vol. 2, 2 vol. xlviii+1761 page(s), ISBN-0 7803 4258 5.

International Search Report, PCT/GB2006/004684, dated May 23, 2007, CXR Ltd.

International Search Report, PCT/US2010/36221, dated Aug. 23, 2010, Rapiscan Security Productions, Inc.

Sheen, David et al. 'Three-Dimensional Millimeter-Wave Imaging for Concealed Weapon Detection', Sep. 2001, IEEE Transactions on Microwave Theory and Techniques, vol. 49, No. 9, pp. 1581-1592.

International Search Report, PCT/GB2004/001731, dated May 27, 2005.

International Search Report, PCT/GB2004/001732, dated Feb. 25, 2005.

International Search Report, PCT/GB2004/001741, dated Mar. 3, 2005.

Keevil, S.V., Lawinski, C.P. and Morton, E.J., 1987, "Measurement of the performance characteristics of anti-scatter grids.", Phys. Med. Biol., 32(3), 397-403.

Morton, E.J., Webb, S., Bateman, J.E., Clarke, L.J. and Shelton, C.G., 1990, "Three-dimensional x-ray micro-tomography for medical and biological applications.", Phys. Med. Biol., 35(7), 805-820.

Morton, E.J., Swindell, W., Lewis, D.G. and Evans, P.M., 1991, "A linear array scintillation-crystal photodiode detector for megavoltage imaging.", Med. Phys., 18(4), 681-691.

Morton, E.J., Lewis, D.G. and Swindell, W., 1988, "A method for the assessment of radiotherapy treatment precision", Brit. J. Radiol., Supplement 22, 25.

Swindell, W., Morton, E.J., Evans, P.M. and Lewis, D.G., 1991, "The design of megavoltage projection imaging systems: some theoretical aspects.", Med. Phys.,18(5), 855-866.

Morton, E.J., Evans, P.M., Ferraro, M., Young, E.F. and Swindell, W., 1991, "A video frame store facility for an external beam radiotherapy treatment simulator.", Brit. J. Radiol., 64, 747-750.

Antonuk, L.E., Yorkston, J., Kim, C.W., Huang, W., Morton, E.J., Longo, M.J. and Street, R.A., 1991, "Light response characteristics of amorphous silicon arrays for megavoltage and diagnostic imaging.", Mat. Res. Soc. Sym. Proc., 219, 531-536.

Yorkston, J., Antonuk, L.E., Morton, E.J., Boudry, J., Huang, W., Kim, C.W., Longo, M.J. and Street, R.A., 1991, "The dynamic response of hydrogenated amorphous silicon imaging pixels.", Mat. Res. Soc. Sym. Proc., 219, 173-178.

Evans, P.M., Gildersleve, J.Q., Morton, E.J., Swindell, W., Coles, R., Ferraro, M., Rawlings, C., Xiao, Z.R. and Dyer, J., 1992, "Image comparison techniques for use with megavoltage imaging systems.", Brit. J. Radiol., 65, 701-709.

Morton, E.J., Webb, S., Bateman, J.E., Clarke, L.J. and Shelton, C.G., 1989, "The development of 3D x-ray micro-tomography at sub 100Å?Aμm resolution with medical, industrial and biological applications.", Presentation at IEE colloquium "Medical scanning and imaging techniques of value in non-destructive testing", London, Nov. 3, 1989.

Antonuk, L.E., Boudry, J., Huang, W., McShan, D.L., Morton, E.J., Yorkston, J, Longo, M.J. and Street, R.A., 1992, "Demonstration of megavoltage and diagnostic x-ray imaging with hydrogenated amorphous silicon arrays.", Med. Phys., 19(6), 1455-1466.

Gildersleve, J.Q., Swindell, W., Evans, P.M., Morton, E.J., Rawlings, C. and Dearnaley, D.P., 1991, "Verification of patient positioning during radiotherapy using an integrated megavoltage imaging system.", in "Tumour Response Monitoring and Treatment Planning", Proceedings of the International Symposium of the W. Vaillant Foundation on Advanced Radiation Therapy, Munich, Germany, Ed A. Breit (Berlin: Springer), 693-695.

(56) References Cited

OTHER PUBLICATIONS

Lewis, D.G., Evans, P.M., Morton, E.J., Swindell, W. and Xiao, X.R., 1992, "A megavoltage CT scanner for radiotherapy verification.", Phys. Med. Biol., 37, 1985-1999.
Antonuk, L.E., Boudry, J., Kim, C.W., Longo, M.J., Morton, E.J., Yorkston, J. and Street, R.A., 1991, "Signal, noise and readout considerations in the development of amorphous silicon photodiode arrays for radiotherapy and diagnostic x-ray imaging.", SPIE vol. 1443 Medical Imaging V: Image Physics, 108-119.
Antonuk, L.E., Yorkston, J., Huang, W., Boudry, J., Morton, E.J., Longo, M.J. and Street, R.A., 1992, "Radiation response characteristics of amorphous silicon arrays for megavoltage radiotherapy imaging.", IEEE Trans. Nucl. Sci., 39,1069-1073.
Antonuk, L.E., Yorkston, J., Huang, W., Boudry, J., Morton, E.J., Longo, M.J. and Street, R.A., 1992, "Factors affecting image quality for megavoltage and diagnostic x-ray a-Si:H imaging arrays.", Mat. Res. Soc. Sym. Proc., 258, 1069-1074.
Antonuk, L.E., Boudry, J., Yorkston, J., Morton, E.J., Huang, W. and Street, R.A., 1992, "Development of thin-film, flat-panel arrays for diagnostic and radiotherapy imaging.", SPIE vol. 1651, Medical Imaging VI: Instrumentation, 94-105.
Yorkston, J., Antonuk, L.E., Seraji, N., Boudry, J., Huang, W., Morton, E.J., and Street, R.A., 1992, "Comparison of computer simulations with measurements from a-Si:H imaging arrays.", Mat. Res. Soc. Sym. Proc., 258, 1163-1168.
Morton, E.J., Antonuk, L.E., Berry, J.E., Boudry, J., Huang, W., Mody, P., Yorkston, J. and Longo, M.J., 1992, "A CAMAC based data acquisition system for flat-panel image array readout", Presentation at IEEE Nuclear Science Symposium, Orlando, Oct. 25-31, 1992.
Antonuk, L.E., Yorkston, J., Huang, W., Boudry, J., Morton, E.J. and Street, R.A., 1993, "Large area, flat-panel a-Si:H arrays for x-ray imaging.", SPIE vol. 1896, Medical Imaging 1993: Physics of Medical Imaging, 18-29.
Morton, E.J., Antonuk, L.E., Berry, J.E., Huang, W., Mody, P. and Yorkston, J., 1994, "A data acquisition system for flat-panel imaging arrays", IEEE Trans. Nucl. Sci., 41(4), 1150-1154.
Antonuk, L.E., Boudry, J., Huang, W., Lam, K.L., Morton, E.J., TenHaken, R.K., Yorkston, J. and Clinthorne, N.H., 1994, "Thin-film, flat-panel, composite imagers for projection and tomographic imaging", IEEE Trans. Med. Im., 13(3), 482-490.
Gilderslev, J., Dearnaley, D., Evans, P., Morton, E.J. and Swindell, W., 1994, "Preliminary clinical performance of a scanning detector for rapid portal imaging", Clin. Oncol., 6, 245-250.
Hess, R., De Antonis, P., Morton, E.J. and Gilboy, W.B., 1994, "Analysis of the pulse shapes obtained from single crystal CdZnTe radiation detectors", Nucl. Inst. Meth., A353, 76-79.
DeAntonis, P., Morton, E.J., T. Menezes, 1996, "Measuring the bulk resistivity of CdZnTe single crystal detectors using a contactless alternating electric field method", Nucl. Inst. Meth., A380, 157-159.
DeAntonis, P., Morton, E.J., Podd, F., 1996, "Infra-red microscopy of CdZnTe radiation detectors revealing their internal electric field structure under bias", IEEE Trans. Nucl. Sci., 43(3), 1487-1490.
Tavora, L.M.N., Morgado, R.E., Estep, R.J., Rawool-Sullivan, M., Gilboy, W.B. and Morton, E.J., 1998, "One-sided imaging of large, dense, objects using the 511 keV photons from induced pair production", IEEE Trans. Nucl. Sci., 45(3), 970-975.
Morton, E.J., 1995, "Archaeological potential of computerised tomography", Presentation at IEE Colloquium on "NDT in archaeology and art", London, May 25, 1995.
Tavora, L.M.N. and Morton, E.J., 1998, "Photon production using a low energy electron expansion of the EGS4 code system", Nucl. Inst. Meth., B143, 253-271.
Patel, D.C. and Morton, E.J., 1998, "Analysis of improved adiabatic pseudo-domino logic family", Electron. Lett., 34(19), 1829-1830.
Kundu, A and Morton, E.J., 1999, "Numerical simulation of argon-methane gas filled proportional counters", Nucl. Inst. Meth., A422, 286-290.
Luggar, R.D., Key, M.J., Morton, E.J. and Gilboy, W.B., 1999, "Energy dispersive X-ray scatter for measurement of oil/water ratios", Nucl. Inst. Meth., A422, 938-941.
Morton, E.J., Crockett, G.M., Sellin, P.J. and DeAntonis, P., 1999, "The charged particle response of CdZnTe radiation detectors", Nucl. Inst. Meth., A422, 169-172.
Morton, E.J., Clark, R.J. and Crowley, C., 1999, "Factors affecting the spectral resolution of scintillation detectors", Nucl. Inst. Meth., A422, 155-158.
Morton, E.J., Caunt, J.C., Schoop, K., Swinhoe, M., 1996, "A new handheld nuclear material analyser for safeguards purposes", Presentation at INMM annual meeting, Naples, Florida, Jul. 1996.
Hepworth, S., McJury, M., Oldham, M., Morton, E.J. and Doran, S.J., 1999, "Dose mapping of inhomogeneities positioned in radiosensitive polymer gels", Nucl. Inst. Meth., A422, 756-760.
Morton, E.J., Luggar, R.D., Key, M.J., Kundu, A., Tavora, L.M.N. and Gilboy, W.B., 1999, "Development of a high speed X-ray tomography system for multiphase flow imaging", IEEE Trans. Nucl. Sci., 46 III(1), 380-384.
Tavora, L.M.N., Morton, E.J., Santos, F.P. and Dias, T.H.V.T., 2000, "Simulation of X-ray tubes for imaging applications", IEEE Trans. Nucl. Sci., 47, 1493-1497.
TÃ?Áj vora, L.M.N., Morton, E.J. and Gilboy, W.B., 2000, "Design considerations for transmission X-ray tubes operated at diagnostic energies", J. Phys. D: Applied Physics, 33(19), 2497-2507.
Morton, E.J., Hossain, M.A., DeAntonis, P. and Ede, A.M.D., 2001, "Investigation of Au-CdZnTe contacts using photovoltaic measurements", Nucl. Inst. Meth., A458, 558-562.
Ede, A.M.D., Morton, E.J. and DeAntonis, P., 2001, "Thin-film CdTe for imaging detector applications", Nucl. Inst. Meth., A458, 7-11.
TÃ?Áj vora, L.M.N., Morton, E.J. and Gilboy, W.B., 2001, "Enhancing the ratio of fluorescence to bremsstrahlung radiation in X-ray tube spectra, App. Rad. and Isotopes, 54(1), 59-72".
Menezes, T. and Morton, E.J., 2001, "A preamplifier with digital output for semiconductor detectors", Nucl. Inst. Meth. A., A459, 303-318.
Johnson, D.R., Kyriou, J., Morton, E.J., Clifton, A.C. Fitzgerald, M. and MacSweeney, J.E., 2001, "Radiation protection in interventional radiology", Clin. Rad., 56(2), 99-106.
Tavora, L.M.N., Gilboy, W.B. and Morton, E.J., 2001, "Monte Carlo studies of a novel X-ray tube anode design", Rad. Phys. and Chem., 61, 527-529.
"Morton, E.J., 1998, "Is film dead: the flat plate revolution", Keynote Talk, IPEM Annual Conference, Brighton, Sep. 14-17, 1998"\.
Luggar, R.D., Morton, E.J., Jenneson, P.M. and Key, M.J., 2001, "X-ray tomographic imaging in industrial process control", Rad. Phys. Chem., 61, 785-787.
Luggar, R.D., Morton, E.J., Key, M.J., Jenneson, P.M. and Gilboy, W.B., 1999, "An electronically gated multi-emitter X-ray source for high speed tomography", Presentation at SPIE Annual Meeting, Denver, Jul. 19-23, 1999.
Gregory, P.J., Hutchinson, D.J., Read, D.B., Jenneson, P.M., Gilboy, W.B. and Morton, E.J., 2001, "Non-invasive imaging of roots with high resolution X-ray microtomography", Plant and Soil, 255(1), 351-359.
Kundu, A., Morton, E.J., Key, M.J. and Luggar, R.D., 1999, "Monte Carlo simulations of microgap gas-filled proportional counters", Presentation at SPIE Annual Meeting, Denver, Jul. 19-23, 1999.
Hossain, M.A., Morton, E.J., and Ozsan, M.E., 2002, "Photoelectronic investigation of CdZnTe spectral detectors", IEEE Trans. Nucl. Sci, 49(4), 1960-1964.
Panman, A., Morton, E.J., Kundu, A and Sellin, P.J., 1999, "Optical Monte Carlo transport in scintillators", Presentation at SPIE Annual Meeting, Denver, Jul. 19-23, 1999.
Jenneson, P.M., Gilboy, W.B., Morton, E.J., and Gregory, P.J., 2003, "An X-ray micro-tomography system optimised for low dose study of living organisms", App. Rad. Isotopes, 58, 177-181.
Key, M.J., Morton, E.J., Luggar, R.D. and Kundu, A., 2003, "Gas microstrip detectors for X-ray tomographic flow imaging", Nucl. Inst. Meth., A496, 504-508.

(56) References Cited

OTHER PUBLICATIONS

Jenneson, P.M., Luggar, R.D., Morton, E.J., Gundogdu, O, and Tuzun, U, 2004, "Examining nanoparticle assemblies using high spatial resolution X-ray microtomography", J. App. Phys, 96(5), 2889-2894.

Tavora, L.M., Gilboy, W.B. and Morton, E.J., 2000, "Influence of backscattered electrons on X-ray tube output", Presentation at SPIE Annual Meeting, San Diego, Jul. 30-Aug. 3, 2000.

Wadeson, N., Morton, E.J., and Lionheart, W.B., 2010, "Scatter in an uncollimated x-ray CT machine based on a Geant4 Monte Carlo simulation", SPIE Medical Imaging 2010: Physics of Medical Imaging, Feb. 15-18, 2010, San Diego, USA.

Morton, E.J., 2010, "Position sensitive detectors in security: Users perspective", Invited talk, STFC meeting on position sensitive detectors, RAL, May 2010.

"FISCAN Multi-power X-ray Luggage Security Check Vehicle", Wenxi Chen, et al., Technique for Police, No. 1, pp. 10-13, 20001231.

International Search Report, PCT/GB2004/001729, dated Aug. 12, 2004, Rapiscan Systems, Inc.

International Search Report, PCT/GB2004/001747, dated Aug. 10, 2004.

International Search Report, PCT/US2011/25777, dated Jul. 26, 2011, Rapiscan Systems, Inc.

International Search Report, PCT/GB2004/001751, dated Mar. 21, 2005.

International Search Report, PCT/US10/36183, dated Aug. 20, 2010.

\* cited by examiner

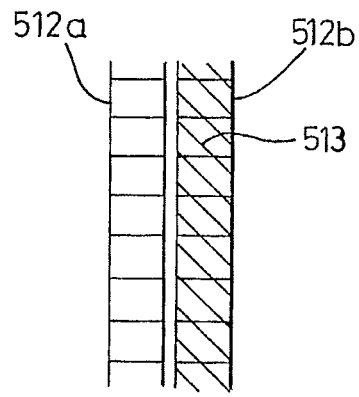
*Fig. 18*
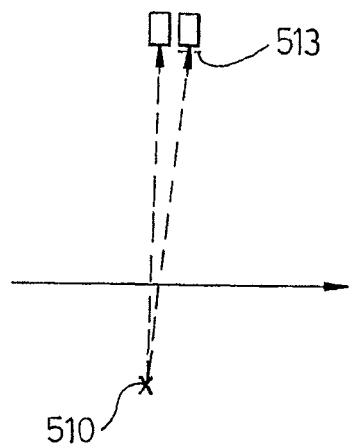
*Fig. 19*
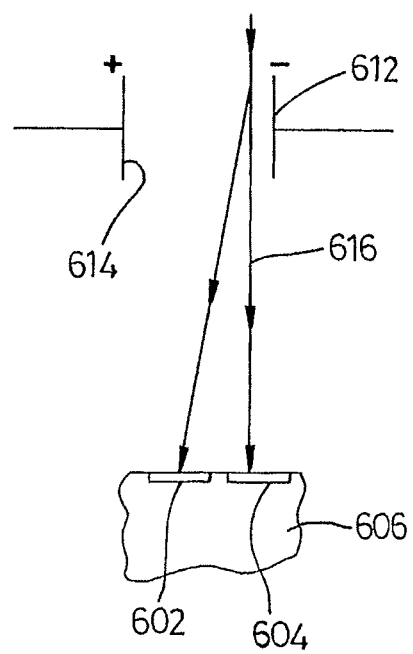
*Fig. 20*
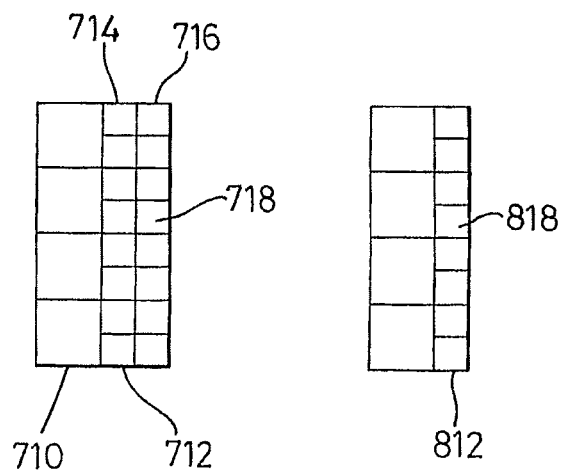
*Fig. 21*    *Fig. 22*

X-RAY TOMOGRAPHIC INSPECTION SYSTEMS FOR THE IDENTIFICATION OF SPECIFIC TARGET ITEMS

CROSS-REFERENCE TO RELATED APPLICATIONS

The present application is a continuation of U.S. patent application Ser. No. 12/787,930, filed on May 26, 2010, now U.S. Pat. No. 8,223,919 which relies on U.S. Patent Provisional Application No. 61/181,068 filed on May 26, 2009, for priority.

U.S. patent application Ser. No. 12/787,930 is also a continuation-in-part of U.S. patent application Ser. No. 12/485,897, filed on Jun. 16, 2009, now abandoned which is a continuation of U.S. patent application Ser. No. 10/554,656, filed on Oct. 25, 2005, and now issued U.S. Pat. No. 7,564,939, which is a 371 national stage application of PCT/GB04/01729, filed on Apr. 23, 2004 and which, in turn, relies on Great Britain Application No. 0309387.9, filed on Apr. 25, 2003, for priority.

U.S. patent application Ser. No. 12/787,930 is also a continuation-in-part of U.S. patent application Ser. No. 12/371,853, filed on Feb. 16, 2009, now U.S. Pat. No. 7,903,789 which is a continuation of U.S. patent application Ser. No. 10/554,975, filed on Oct. 25, 2005, and now issued U.S. Pat. No. 7,512,215, which is a 371 national stage application of PCT/GB2004/01741, filed on Apr. 23, 2004 and which, in turn, relies on Great Britain Application Number 0309383.8, filed on Apr. 25, 2003, for priority.

U.S. patent application Ser. No. 12/787,930 is also a continuation-in-part of U.S. patent application Ser. No. 12/651,479, filed on Jan. 3, 2010, now abandoned which is a continuation of U.S. patent application Ser. No. 10/554,654, filed on Oct. 25, 2005, and now issued U.S. Pat. No. 7,664,230, which is a 371 national stage application of PCT/GB2004/001731, filed on Apr. 23, 2004 and which, in turn, relies on Great Britain Patent Application Number 0309371.3, filed on Apr. 25, 2003, for priority.

U.S. patent application Ser. No. 12/787,930 is also a continuation-in-part of U.S. patent application Ser. No. 12/364,067, filed on Feb. 2, 2009, now abandoned which is a continuation of U.S. patent application Ser. No. 12/033,035, filed on Feb. 19, 2008, and now issued U.S. Pat. No. 7,505,563, which is a continuation of U.S. patent application Ser. No. 10/554,569, filed on Oct. 25, 2005, and now issued U.S. Pat. No. 7,349,525, which is a 371 national stage filing of PCT/GB04/001732, filed on Apr. 23, 2004 and which, in turn, relies on Great Britain Patent Application Number 0309374.7, filed on Apr. 25, 2003, for priority.

U.S. patent application Ser. No. 12/787,930 is also a continuation-in-part of U.S. patent application Ser. No. 12/758,764, filed on Apr. 12, 2010, now U.S. Pat. No. 7,929,663 which is a continuation of U.S. patent application Ser. No. 12/211,219, filed on Sep. 16, 2008, and now issued U.S. Pat. No. 7,724,868, which is a continuation of U.S. patent Ser. No. 10/554,655, filed on Oct. 25, 2005, and now issued U.S. Pat. No. 7,440,543, which is a 371 national stage application of PCT/GB2004/001751, filed on Apr. 23, 2004, and which, in turn, relies on Great Britain Patent Application Number 0309385.3, filed on Apr. 25, 2003, for priority.

U.S. patent application Ser. No. 12/787,930 is also a continuation-in-part of U.S. patent application Ser. No. 12/697,073, filed on Jan. 29, 2010, now U.S. Pat. No. 8,085,897 which is a continuation of U.S. patent application Ser. No. 10/554,570, filed on Oct. 25, 2005, and now issued U.S. Pat. No. 7,684,538, which is a 371 national stage application of PCT/GB2004/001747, filed on Apr. 23, 2004, and which, in turn, relies on Great Britain Patent Application Number 0309379.6, filed on Apr. 25, 2003, for priority.

U.S. patent application Ser. No. 12/787,930 is also a continuation-in-part of U.S. patent application Ser. No. 12/097,422, filed on Jun. 13, 2008, now U.S. Pat. No. 7,876,879 and U.S. patent application Ser. No. 12/142,005, filed on Jun. 19, 2008, now U.S. Pat. No. 8,135,110 both of which are 371 national stage applications of PCT/GB2006/004684, filed on Dec. 15, 2006, which, in turn, relies on Great Britain Patent Application Number 0525593.0, filed on Dec. 16, 2005, for priority.

U.S. patent application Ser. No. 12/787,930 is also a continuation-in-part of U.S. patent application Ser. No. 12/478,757, filed on Jun. 4, 2009, now U.S. Pat. No. 8,094,784 which is a continuation of U.S. patent application Ser. No. 12/364,067, filed on Feb. 2, 2009, now abandoned which is a continuation of U.S. patent application Ser. No. 12/033,035, filed on Feb. 19, 2008, and now issued U.S. Pat. No. 7,505,563, which is a continuation of U.S. patent application Ser. No. 10/554,569, filed on Oct. 25, 2005, and now issued U.S. Pat. No. 7,349,525, which is a 371 national stage filing of PCT/GB04/001732, filed on Apr. 23, 2004 and which, in turn, relies on Great Britain Patent Application Number 0309374.7, filed on Apr. 25, 2003, for priority. In addition, U.S. Patent Application number relies on Great Britain Patent Application Number 0812864.7, filed on Jul. 15, 2008, for priority.

U.S. patent application Ser. No. 12/787,930 is also a continuation-in part of U.S. patent application Ser. No. 12/712,476, filed on Feb. 25, 2010, now U.S. Pat. No. 8,243,876 which relies on U.S. Provisional Patent Application No. 61/155,572 filed on Feb. 26, 2009 and Great Britain Patent Application No. 0903198.0 filed on Feb. 25, 2009, for priority.

Each of the aforementioned PCT, foreign, and U.S. applications, and any applications related thereto, is herein incorporated by reference in their entirety.

FIELD

The present application relates to X-ray scanning and, particularly to the security screening of baggage, packages and other suspicious objects, such as sharp objects, knives, nuclear materials, tobacco, currency, narcotics, and liquids.

BACKGROUND

X-ray computed tomography (CT) scanners have been used in security screening in airports for several years. A conventional system comprises an X-ray tube that is rotated about an axis with an arcuate X-ray detector that is rotated at the same speed around the same axis. The conveyor belt on which the baggage is carried is placed within a suitable aperture around the central axis of rotation, and moved along the axis as the tube is rotated. A fan-beam of X-radiation passes from the source through the object to be inspected to the X-ray detector array.

The X-ray detector array records the intensity of X-rays passed through the object to be inspected at several locations along its length. One set of projection data is recorded at each of a number of source angles. From these recorded X-ray intensities, it is possible to form a tomographic (cross-sectional) image, typically by means of a filtered back projection algorithm. In order to produce an accurate tomographic image of an object, such as a bag or package, it can be shown that there is a requirement that the X-ray source pass through every plane through the object. In the arrangement described above, this is achieved by the rotational scanning of the X-ray source, and the longitudinal motion of the conveyor on which the object is carried.

In this type of system the rate at which X-ray tomographic scans can be collected is dependent on the speed of rotation of the gantry that holds the X-ray source and detector array. In a modern CT gantry, the entire tube-detector assembly and gantry will complete two to four revolutions per second. This allows up to four or eight tomographic scans to be collected per second respectively.

As the state-of-the-art has developed, the single ring of X-ray detectors has been replaced by multiple rings of detectors. This allows many slices (typically 8) to be scanned simultaneously and reconstructed using filtered back projection methods adapted from the single scan machines. With a continuous movement of the conveyor through the imaging system, the source describes a helical scanning motion about the object. This allows a more sophisticated cone-beam image reconstruction method to be applied that can in principle offer a more accurate volume image reconstruction.

In a further development, swept electron beam scanners have been demonstrated in medical applications whereby the mechanical scanning motion of the X-ray source and detectors is eliminated, being replaced by a continuous ring (or rings) of X-ray detectors that surround the object under inspection with a moving X-ray source being generated as a result of sweeping an electron beam around an arcuate anode. This allows images to be obtained more rapidly than in conventional scanners. However, because the electron source lies on the axis of rotation, such swept beam scanners are not compatible with conveyor systems which themselves pass close, and parallel, to the axis of rotation.

There is still a need for methods and systems that enable the rapid generation of tomographic images that have the capability of detecting certain items of interest, including liquids, narcotics, currency, tobacco, nuclear materials, sharp objects, and fire-arms.

SUMMARY OF THE INVENTION

The present invention provides an X-ray scanning system for inspecting items, the system comprising an X-ray source extending around a scanning volume, and defining a plurality of source points from which X-rays can be directed through the scanning volume, an X-ray detector array also extending around the scanning volume and arranged to detect X-rays from the source points which have passed through the scanning volume and produce output signals dependent on the detected X-rays, and a conveyor arranged to convey the items through the scanning volume.

The present invention further provides a networked inspection system comprising an X-ray scanning system, a workstation and connection means arranged to connect the scanning system to the workstation, the scanning system comprising an X-ray source extending around a scanning volume, and defining a plurality of source points from which X-rays can be directed through the scanning volume, an X-ray detector array also extending around the scanning volume and arranged to detect X-rays from the source points which have passed through the scanning volume and produce output signals dependent on the detected X-rays, and a conveyor arranged to convey the items through the scanning volume.

The present invention further provides a sorting system for sorting items, the system comprising a tomographic scanner arranged to scan a plurality of scanning regions of each item thereby to produce a scanner output, analyzing means arranged to analyze the scanner output and allocate each item to one of a plurality of categories at least partly on the basis of the scanner output, and sorting means arranged to sort items at least partly on the basis of the categories to which they have been allocated.

The present invention further provides an X-ray scanning system comprising an X-ray source arranged to generate X-rays from a plurality of X-ray source positions around a scanning region, a first set of detectors arranged to detect X-rays transmitted through the scanning region, a second set of detectors arranged to detect X-rays scattered within the scanning region, and processing means arranged to process outputs from the first set of detectors to generate image data which defines an image of the scanning region, to analyze the image data to identify an object within the image, and to process the outputs from the second set of detectors to generate scattering data, and to associate parts of the scattering data with the object.

The present invention further provides a data collecting system for collecting data from an X-ray scanner, the system comprising a memory having a plurality of areas each being associated with a respective area of an image, data input means arranged to receive input data from a plurality of X-ray detectors in a predetermined sequence, processing means arranged to generate from the input data X-ray transmission data and X-ray scattering data associated with each of the areas of the image, and to store the X-ray transmission data and the X-ray scattering data in the appropriate memory areas.

The present invention further provides an X-ray scanning system comprising a scanner arranged to scan an object to generate scanning data defining a tomographic X-ray image of the object, and processing means arranged to analyze the scanning data to extract at least one parameter of the image data and to allocate the object to one of a plurality of categories on the basis of the at least one parameter.

In an embodiment, the present invention provides an X-ray scanning system comprising a scanner arranged to scan an object to generate scanning data defining a tomographic X-ray image of the object, and processing means arranged to analyse the scanning data to extract at least one parameter of the image data and to allocate the object to one of a plurality of categories on the basis of the at least one parameter. The processing means comprise: one or more parameter extractors for identifying one or more predefined features in the tomographic X-ray image, the identified features being low level parameters of the X-ray image; each parameter extractor being arranged to perform a different processing operation to determine a different parameter; one or more decision trees for constructing high level parameters by analyzing the identified low level parameters of the X-ray image; and a database searcher for mapping the X-ray image of the object as one of 'threat-causing' or 'clear' by using the constructed high level parameters of the X-ray image and predefined data stored in a database coupled with the database searcher. The parameter extractors are designed to operate on one of 2-dimensional images, 3-dimensional images and sinogram image data.

In another embodiment, the present invention provides a method for detecting a predefined material by using an X-ray scanning system comprising a scanner arranged to scan an object to generate a tomographic X-ray image of the object, and processing means arranged to analyse the scanning data to extract at least one parameter of the image data and to allocate the object to one of a plurality of categories on the basis of the at least one parameter. The method comprises the steps of: configuring a plurality of parameter extractors for identifying one or more predefined features in the tomographic X-ray image, the identified features being low level parameters of the X-ray image; configuring one or more decision trees for constructing high level parameters by analyzing the identified low level parameters of the X-ray image; identifying the object as the predefined material by mapping the constructed high level parameters of the X-ray image with stored data defining the material. The method further comprises the step of classifying the X-ray image of the object as one of 'threat-causing' or 'clear' by mapping the constructed high level parameters of the X-ray image with predefined stored data.

In an embodiment, the present invention provides a method for detecting a liquid wherein the steps of configuring a plurality of parameter extractors for identifying one or more predefined features in the tomographic X-ray image and configuring one or more decision trees for constructing high level parameters by analyzing the identified low level parameters of the X-ray image comprise the steps of: configuring a first parameter extractor to process the X-ray image to identify: the object being scanned; an outer envelope defining the object being scanned, and one or more flat surfaces within an outer envelope of the object being scanned; configuring a second parameter extractor to locate a contiguous volume of a material of uniform density extending from each identified flat surface in a vertical direction;

and configuring a decision tree for: calculating the volume of the contiguous volume of material located; assigning the calculated volume to at least one predetermined shape corresponding to one of an oval bottle, a rectangular bottle and a triangular bottle; calculating a mean reconstructed density of the contiguous volume; and transferring the parameters corresponding to volume, shape and density for identification of the liquid by mapping against a database.

In another embodiment, the present invention provides a method for detecting a narcotic wherein, the steps of configuring a plurality of parameter extractors for identifying one or more predefined features in the tomographic X-ray image and configuring one or more decision trees for constructing high level parameters by analyzing the identified low level parameters of the X-ray image comprise the steps of: configuring a first parameter extractor to process the X-ray image to identify contiguous volumes of low density material in at least sheet and bulk shapes; configuring a second parameter extractor to processes the identified contiguous volumes to determine statistical properties of the contiguous volumes; configuring a third parameter extractor for identifying one or more collections of randomly oriented parts of small volume; and configuring a decision tree for correlating the parameters corresponding to volume shape and statistical properties identified by a plurality of parameter extractors; and transferring the correlated data for identification of the narcotic material by mapping against a database.

In yet another embodiment, the present invention provides a method for detecting a currency wherein, the steps of configuring a plurality of parameter extractors for identifying one or more predefined features in the tomographic X-ray image and configuring one or more decision trees for constructing high level parameters by analyzing the identified low level parameters of the X-ray image comprise the steps of: configuring a first parameter extractor to identify one or more "bow-tie" shaped features in the X-ray image; configuring a second parameter extractor to identify one or more rectangular shapes in multiples of predefined physical dimension of predefined denominations of currency; configuring a third parameter extractor for identifying repeating patterns in the parameters identified by the first and the second parameter extractors; configuring a fourth parameter extractor for generating statistical properties of the patterns identified by the first, the second and the third parameter extractors; and configuring a decision tree for correlating the parameters identified by a plurality of parameter extractors; and transferring the correlated data for identification of the currency by mapping against a database.

In yet another embodiment, the present invention provides a method for detecting cigarettes wherein, the steps of configuring a plurality of parameter extractors for identifying one or more predefined features in the tomographic X-ray image and configuring one or more decision trees for constructing high level parameters by analyzing the identified low level parameters of the X-ray image comprise the steps of: configuring a first parameter extractor to identify repeating array structures with a length and width dimension consistent with predefined dimensions of cigarettes; configuring a second parameter extractor to identify rectangular volumes of predefined aspect ratio matching that of predefined cigarette packaging with a density that is consistent with predefined brands of cigarettes; and configuring a decision tree for correlating the parameters identified by a plurality of parameter extractors; and transferring the correlated data for identification of the cigarettes by mapping against a database.

In yet another embodiment, the present invention provides a method for detecting a special nuclear material or a shielded radioactive source wherein, the steps of configuring a plurality of parameter extractors for identifying one or more predefined features in the tomographic X-ray image and configuring one or more decision trees for constructing high level parameters by analyzing the identified low level parameters of the X-ray image comprise the steps of: configuring a first parameter extractor to identify highly attenuating regions in the X-ray image where the reconstructed pixel intensity is above a predefined threshold value; and configuring a decision tree for: determining whether the attenuating region is part of a larger structure; evaluating at least a shape, a location and a size of the attenuating region if it is determined that the attenuating region is not a part of a larger structure; and transferring the evaluated parameters corresponding to the attenuating region for identification of the special nuclear material or a shielded radioactive source by mapping against a database.

In yet another embodiment, the present invention provides a method for detecting a pointed object or a knife wherein, the steps of configuring a plurality of parameter extractors for identifying one or more predefined features in the tomographic X-ray image and configuring one or more decision trees for constructing high level parameters by analyzing the identified low level parameters of the X-ray image comprise the steps of: configuring a first parameter extractor to detect one or more protruding points in the X-ray image; configuring a second parameter extractor to identify one or more blades having a predefined length to width aspect ratio; configuring a third parameter extractor for identifying folded blades having a repeating structure of at least two air gaps and three material fills; and configuring a decision tree for correlating the parameters identified by a plurality of parameter extractors; and transferring the correlated data for identification of the pointed object or knife by mapping against a database.

In yet another embodiment, the present invention provides a method for detecting a fire arm wherein, the steps of configuring a plurality of parameter extractors for identifying one or more predefined features in the tomographic X-ray image and configuring one or more decision trees for constructing high level parameters by analyzing the identified low level parameters of the X-ray image comprise the steps of: configuring a first parameter extractor to identify one or more cylindrical metal tubes in the X-ray image; configuring a second parameter extractor to identify one or more trigger mechanism and firing pin; configuring a third parameter extractor for identifying high density slugs and bullets with composition ranging from aluminium (density 2.7 g/cm3) to lead (density >11 g/cm3); and configuring a decision tree for correlating the parameters identified by a plurality of parameter extractors and associated data; and transferring the correlated data for identification of the currency by mapping against a database.

In another embodiment, the present invention is an X-ray scanning system comprising: a non-rotating X-ray scanner that generates scanning data defining a tomographic X-ray image of the object; a processor executing programmatic instructions wherein said executing processor analyzes the scanning data to extract at least one parameter of the tomographic X-ray image and wherein said processor is configured to determine if said object is a bottle containing a liquid, a narcotic, tobacco, fire-arms, currency, sharp objects, or any other illicit object. The processor executes programmatic instructions to allocate the object to one of a plurality of categories on the basis of the at least one parameter. The programmatic instructions comprise at least one parameter extractor for identifying at least one predefined feature in the tomographic X-ray image wherein said predefined feature comprises a plurality of low level parameters of the X-ray image. Such low level parameters can include basic dimension, density, size, and shape information.

The programmatic instructions comprise at least one decision tree for constructing high level parameters based upon the identified low level parameters of the X-ray image. The high level parameters include determinations of the type of object, such as a bottle, repeating patterns, arrays of structures, among other defining variables. The X-ray scanning system further comprises a database search tool for mapping the constructed high level parameters of the X-ray image to predefined data stored in a database. The X-ray scanning system further comprises an alarm system for activating an alarm based on a result of said mapping, wherein said alarm defines an object as being a potential threat or not a potential threat. The at least one parameter extractor is configured to operate on one 2-dimensional images, 3-dimensional images or sinogram image data.

In various embodiments, the methods of the present invention described above are provided as a computer readable medium tangibly embodying a program of machine-readable instructions executable by a processor.

BRIEF DESCRIPTION OF THE INVENTION

Embodiments of the present invention will now be described by way of example only with reference to the accompanying drawings in which:

FIG. 18 is a partial view of a dual energy scanner according to a further embodiment of the invention;

FIG. 19 is a further partial view of the scanner of FIG. 18;

FIG. 20 is a schematic view of a dual energy X-ray source of a further embodiment of the invention;

FIG. 21 is a schematic view of a detector array of a scanner according to a further embodiment of the invention;

FIG. 22 is a schematic view of a detector array of a scanner according to a further embodiment of the invention;

DETAILED DESCRIPTION OF THE INVENTION

Figure 1:
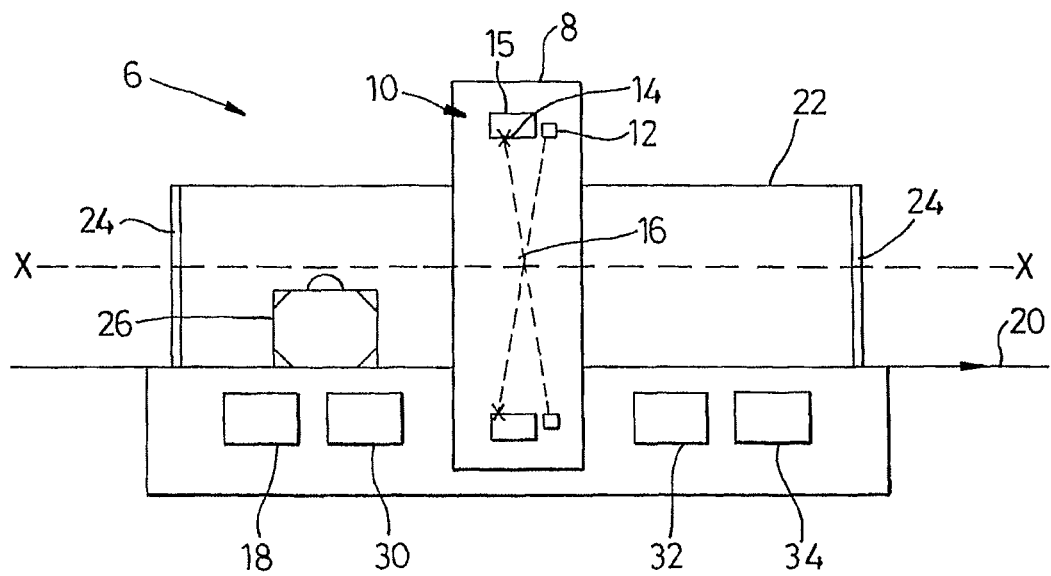
FIG. 1 is a longitudinal section of a real time tomography security scanning system according to a first embodiment of the invention.
Figure 2:
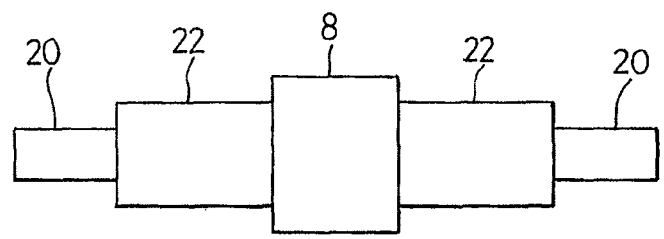
FIG. 2 is a plan view of the system of FIG. 1.
Figure 3:
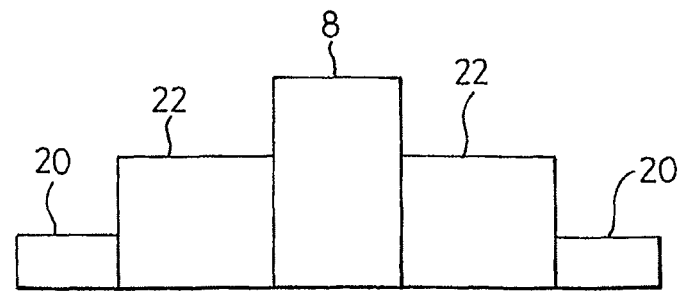
FIG. 3 is a schematic side view of the system of FIG. 1.

Referring to FIGS. 1 to 3, a concourse baggage scanning system 6 comprises a scanning unit 8 comprising a multi-focus X-ray source 10 and X-ray detector array 12. The source 10 comprises a large number of source points 14 in respective spaced locations on the source, and arranged in a full 360.degree circular array around the axis X-X of the system. It will be appreciated that arrays covering less than the full 360.degree. angle can also be used.

Figure 1A:
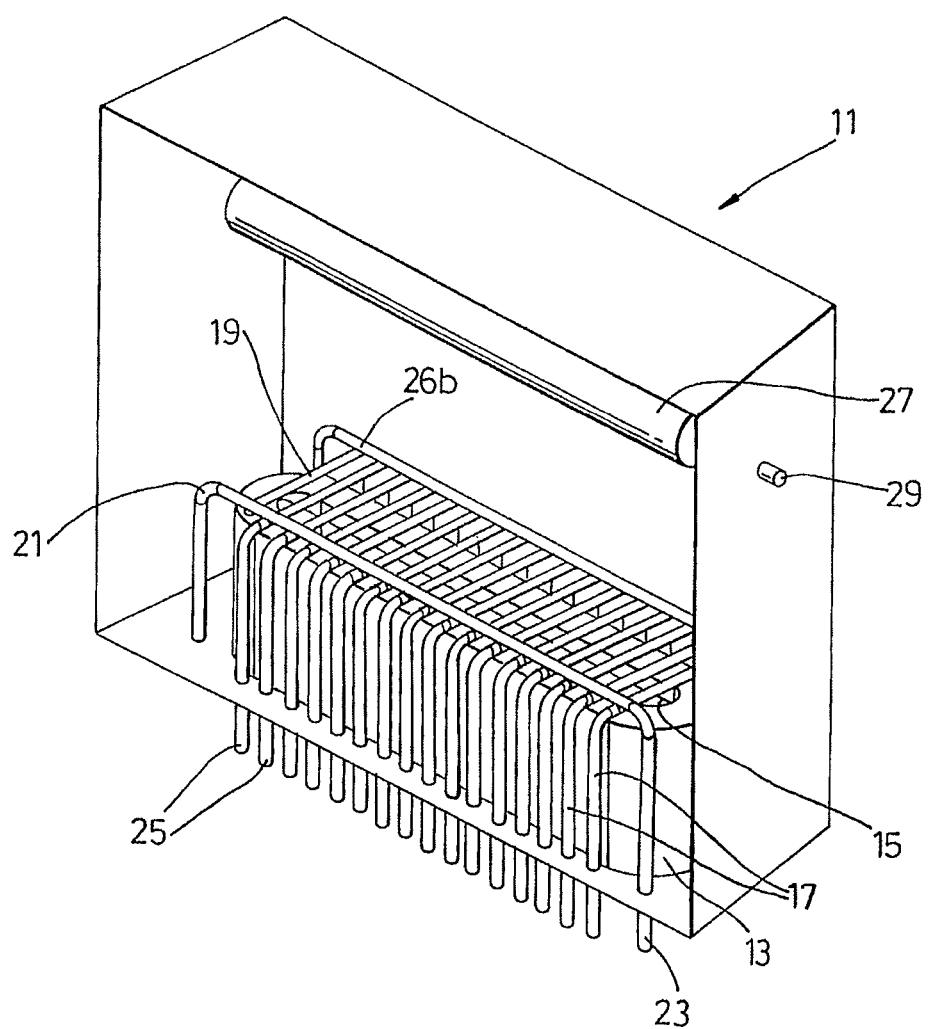
FIG. 1a is a perspective view of an X-ray source of the system of FIG. 1.

Referring to FIG. 1a, the X-ray source 10 is made up of a number of source units 11 which are spaced around the scanning region 16 in a substantially circular arrangement, in a plane perpendicular to the direction of movement of the conveyor. Each source unit 11 comprises a conductive metal suppressor 13 having two sides and an emitter element 15 extending along between the suppressor sides. A number of grid elements in the form of grid wires 17 are supported above the suppressor 13 perpendicular to the emitter element 15. A number of focusing elements in the form of focusing wires 19 are supported in another plane on the opposite side of the grid wires to the emitter element. The focusing wires 19 are parallel to the grid wires 17 and spaced apart from each other with the same spacing as the grid wires, each focusing wire 19 being aligned with a respective one of the grid wires 17.

The focusing wires 19 are supported on two support rails 21 which extend parallel to the emitter element 15, and are spaced from the suppressor 13. The support rails 21 are electrically conducting so that all of the focusing wires 19 are electrically connected together. One of the support rails 21 is connected to a connector 23 to provide an electrical connection for the focusing wires 19. Each of the grid wires 17 extends down one side of the suppressor 12 and is connected to a respective electrical connector 25 which provide separate electrical connections for each of the grid wires 17.

An anode 27 is supported above the grid wires 17 and focusing wires 19. The anode 27 is formed as a rod, typically of copper with tungsten or silver plating, and extends parallel to the emitter element 15. The grid and focusing wires 17, 19 therefore extend between the emitter element 15 and the anode 27. An electrical connector 29 provides an electrical connection to the anode 27.

The grid wires 17 are all connected to a negative potential, apart from two which are connected to a positive potential. These positive grid wires extract a beam of electrons from an area of the emitter element 15 and, with focusing by the focusing wires 19, direct the electron beam at a point on the anode 27, which forms the X-ray source point for that pair of grid wires. The potential of the grid wires can therefore be switched to select which pair of grid wires is active at any one time, and therefore to select which point on the anode 27 is the active X-ray source point at any time.

The source 10 can therefore be controlled to produce X-rays from each of the source points 14 in each of the source units 11 individually and, referring back to FIG. 1, X-rays from each source point 14 are directed inwards through the scanning region 16 within the circular source 10. The source 10 is controlled by a control unit 18 which controls the electrical potentials applied to the grid wires 17 and hence controls the emission of X-rays from each of the source points 14. Other suitable X-ray source designs are described in WO 2004/097889.

The multi-focus X-ray source 10 allows the electronic control circuit 18 to be used to select which of the many individual X-ray source points 14 within the multi-focus X-ray source is active at any moment in time. Hence, by electronically scanning the multi-focus X-ray tube, the illusion of X-ray source motion is created with no mechanical parts physically moving. In this case, the angular velocity of source rotation can be increased to levels that simply cannot be achieved when using conventional rotating X-ray tube assemblies. This rapid rotational scanning translates into an equivalently speeded up data acquisition process and subsequently fast image reconstruction.

The detector array 12 is also circular and arranged around the axis X-X in a position that is slightly offset in the axial direction from the source 10. The source 10 is arranged to direct the X-rays it produces through the scanning region 16 towards the detector array 12 on the opposite side of the scanning region. The paths 18 of the X-ray beams therefore pass through the scanning region 16 in a direction that is substantially, or almost, perpendicular to the scanner axis X-X, crossing each other near to the axis. The volume of the scanning region that is scanned and imaged is therefore in the form of a thin slice perpendicular to the scanner axis. The source is scanned so that each source point emits X-rays for a respective period, the emitting periods being arranged in a predetermined order. As each source point 14 emits X-rays, the signals from the detectors 12, which are dependent on the intensity of the X-rays incident on the detector, are produced, and the intensity data that the signals provide are recorded in memory. When the source has completed its scan the detector signals can be processed to form an image of the scanned volume.

A conveyor belt 20 moves through the imaging volume, from left to right, as seen in FIG. 1, parallel to the axis X-X of the scanner. X-ray scatter shields 22 are located around the conveyor belt 20 upstream and downstream of the main X-ray system to prevent operator dose due to scattered X-rays. The X-ray scatter shields 22 include lead rubber strip curtains 24 at their open ends such that the item 26 under inspection is dragged through one curtain on entering, and one on leaving, the inspection region. In the integrated system shown, the main electronic control system 18, a processing system 30, a power supply 32 and cooling racks 34 are shown mounted underneath the conveyor 20. The conveyor 20 is arranged to be operated normally with a continuous scanning movement at constant conveyor speed, and typically has a carbon-fiber frame assembly within the imaging volume.

Figure 4:
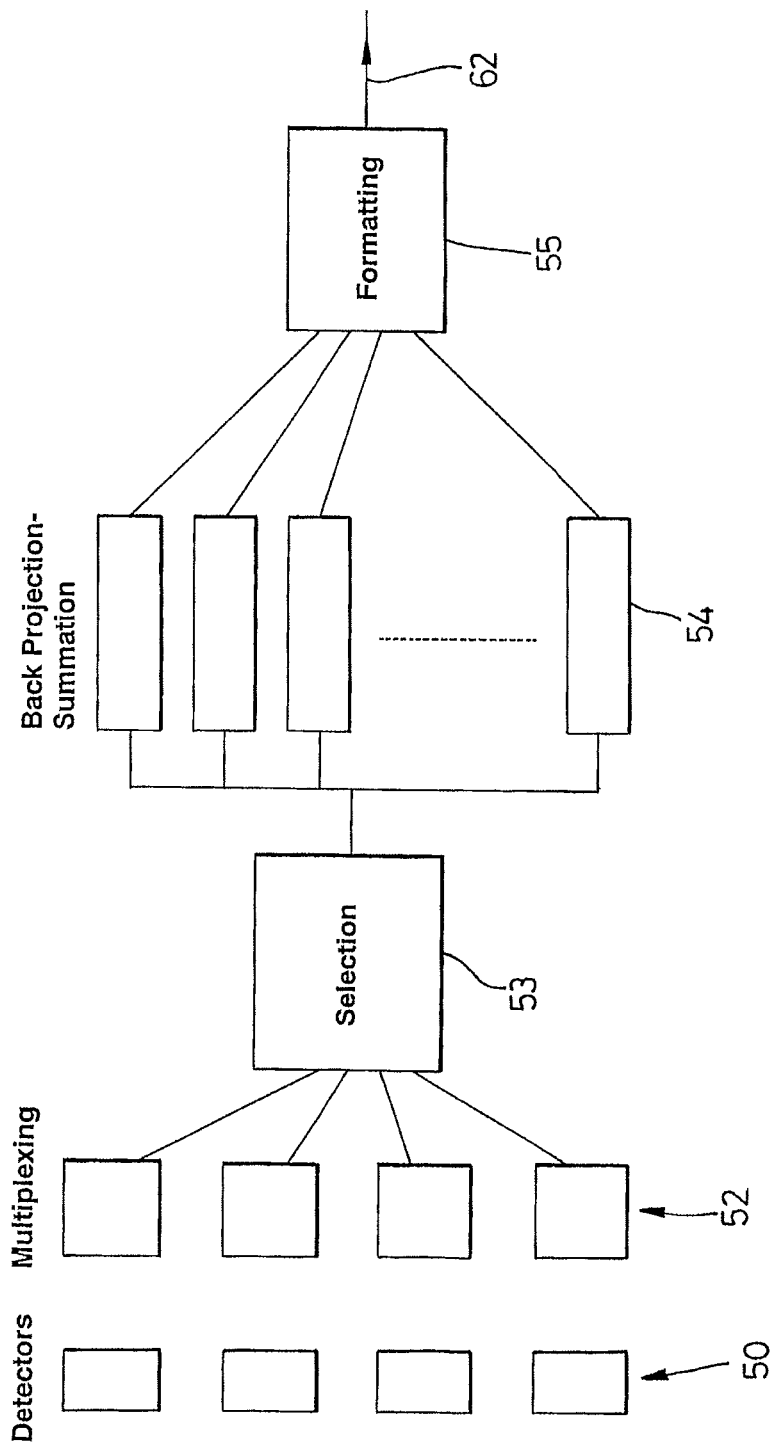
FIG. 4 is a schematic diagram of a data acquisition system forming part of the system of FIG. 1.

Referring to FIG. 4 the processing system 30 includes an electronic data acquisition system and real-time image reconstruction system. The X-ray detector array 12 comprises banks of individual X-ray detectors 50 configured in a simple linear pattern (e.g. 1.times.16). Multiple ring patterns (e.g. 8.times.16) are also possible. Each detector 50 outputs a signal dependent on the intensity of the X-rays it detects. A multiplexing block 52 multiplexes the output data signals from each of the input X-ray detectors 50, performs data filtering, gain and offset corrections and formats the data into a high-speed serial stream. A selection block 53 takes input from all of the multiplexing blocks 52 and selects just the part of the entire X-ray data that is required for the image reconstruction. The selection block 53 also determines the un-attenuated X-ray beam intensity, Io, for the appropriate X-ray source point (which will vary for every X-ray source point within the multi-focus X-ray tube), processes the X-ray intensity data, Ix, from the multiplexing block 52 by forming the result $\log_o(Ix/Io)$ and then convolves this with a suitable 1-D filter. The resulting projection data is recorded as a sinogram, in which the data is arranged in an array with pixel number along one axis, in this case horizontally, and source angle along another axis, in this case vertically.

Data is then passed from the selection block 53 in parallel to a set of back projection-summation processor elements 54. The processor elements 54 are mapped into hardware, using look-up tables with pre-calculated coefficients to select the necessary convolved X-ray data and weighting factors for fast back projection and summation. A formatting block 55 takes the data representing individual reconstructed image tiles from the multiple processor elements 54 and formats the final output image data to a form suitable for generating a suitably formatted three dimensional image on a display screen. This output can be generated fast enough for the images to be generated in real time, for viewing in real time or off-line, hence the system is termed a real time tomography (RTT) system.

In this embodiment the multiplexing block 52 is coded in software, the selection block 53 and formatting block 55 are both coded in firmware, and the processor elements mapped in hardware. However, each of these components could be either hardware or software depending on the requirements of the particular system.

Figure 5:
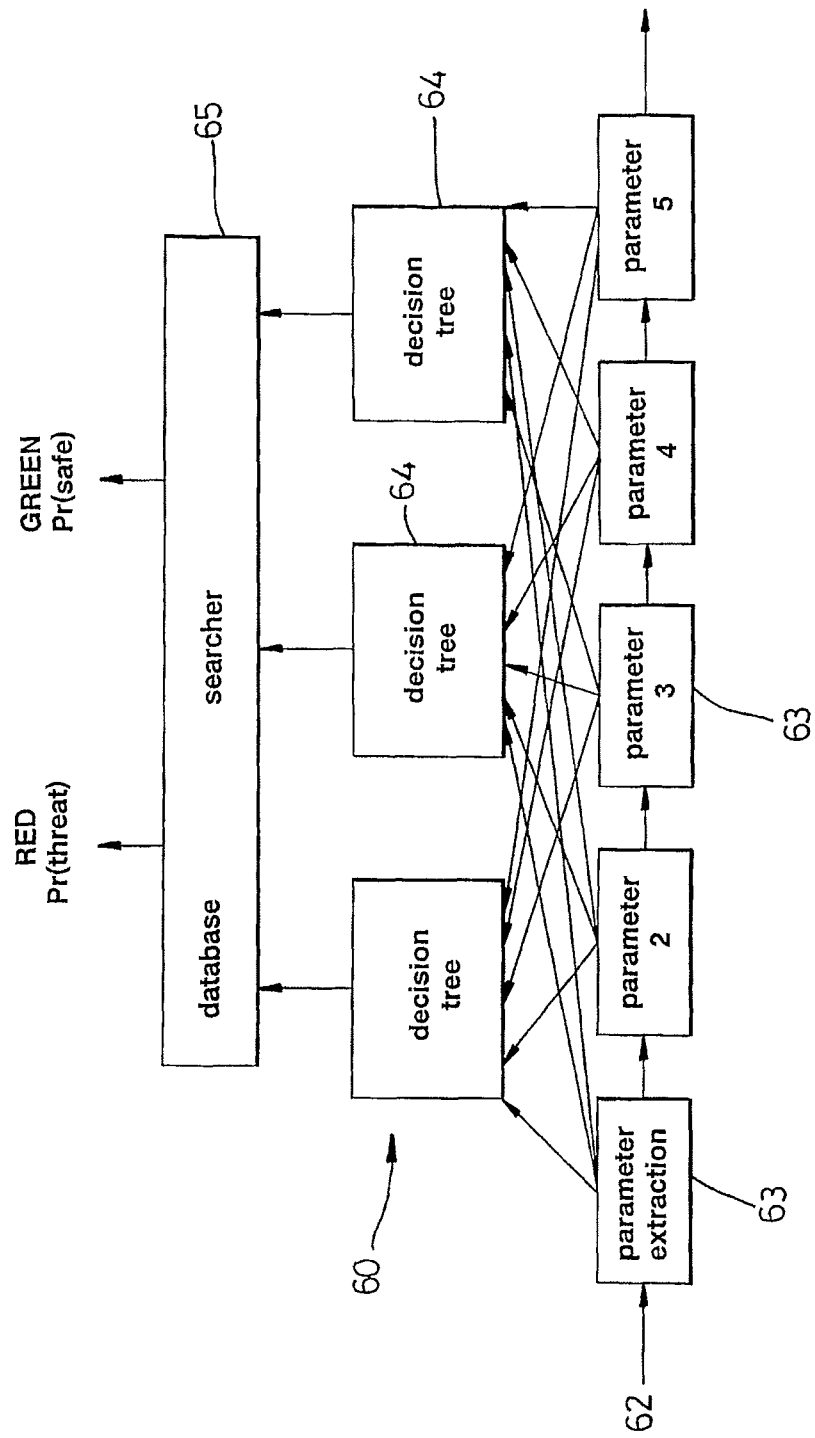
FIG. 5 is a schematic diagram of a threat detection system forming part of the system of FIG. 1.

Referring to FIG. 5 each of the final output images for each baggage item is then processed by a threat detection processor 60 within the processing system 30 which is arranged to determine whether the imaged baggage item represents a threat. In the threat detection processor 60, input X-ray tomographic image data 62 is passed in to a set of low-level parameter extractors 63 (level 1). The parameter extractors 63 identify features in the image such as areas of constant grey level, texture and statistics. Some of the extractors work on the data for individual 2 dimensional images or slices, some work on the 3 dimensional images, and some work on the sinogram data. Where possible, each extractor works in parallel on the same set of input data, and each extractor is arranged to perform a different processing operation and to determine a different parameter. At the end of the processing, the parameters determined by the parameter extractors 63 are passed up to a set of decision trees 64 (level 2). Details of the parameters extracted are given below. The decision trees 64 each take a number (typically all) of the low level parameters and construct respective higher level information, such as information regarding contiguous volumes, with associated statistics. At the top level (level 3), a database searcher 65 maps the higher level parameters produced at level 2 into a 'red' probability Pr(threat) of there being a threat present and a 'green' probability Pr(safe) of the item under inspection being safe. These probabilities are used by the processing system 30 to allocate the scanned item to an appropriate safety category, and to produce an automatic sorting control output. This automatic sorting control output can be either a first 'green' output indicating that the item is allocated to a clear category, a second 'red' output indicating that the item is allocated to a 'not clear' category, or a third 'amber' output indicating that the automatic sorting cannot be carried out with sufficient reliability to allocated the item to the 'clear' or the 'not clear' category. Specifically if Pr(safe) is above a predetermined value, (or Pr(threat) is below a predetermined value) then the automatic sorting output will be produced having a first signal form, indicating that the item should be allocated to the green channel. If Pr(threat) is above a predetermined value, (or Pr(safe) is below a predetermined value) then the automatic sorting output will be produced having a second signal form, indicating that the item should be allocated to the red channel. If Pr(threat) (or Pr(safe)) is between the two predetermined values, then the automatic sorting output is produced having a third signal form, indicating that the item cannot be allocated to either the red or green channel. The probabilities can also be output as further output signals.

The parameters that will be determined by the parameter extractors 63 generally relate to statistical analysis of pixels within separate regions of the 2-dimensional or 3-dimensional image. In order to identify separate regions in the image a statistical edge detection method is used. This starts at a pixel and then checks whether adjacent pixels are part of the same region, moving outwards as the region grows. At each step an average intensity of the region is determined, by calculating the mean intensity of the pixels within the region, and the intensity of the next pixel adjacent to the region is compared to that mean value, to determine whether it is close enough to it for the pixel to be added to the region. In this case the standard deviation of the pixel intensity within the region is determined, and if the intensity of the new pixel is within the standard deviation, then it is added to the region. If it is not, then it is not added to the region, and this defines the edge of the region as being the boundary between pixels in the region and pixels that have been checked and not added to the region.

Once the image has been divided into regions, then parameters of the region can be measured. One such parameter is a measure of the variance of the pixel intensity within the region. If this is high this might be indicative of a lumpy material, which might for example be found in a home-made bomb, while if the variance is low this would be indicative of a uniform material such as a liquid.

Another parameter that is measured is the skewedness of the distribution of pixel value within the region, which is determined by measuring the skewedness of a histogram of pixel values. A Gaussian, i.e. non-skewed, distribution indicates that the material within the region is uniform, whereas a more highly skewed distribution indicates non-uniformities in the region.

As described above, these low-level parameters are passed up to the decision trees 64, where higher level information is constructed and higher level parameters are determined. One such higher level parameter is the ratio of the surface area to the volume of the identified region. Another is a measure of similarity, in this case cross-correlation, between the shape of the region and template shapes stored in the system. The template shapes are arranged to correspond to the shape of items that pose a security threat, such as guns or detonators. These high level parameters are used as described above to determine a level if threat posed by the imaged object.

Figure 6:
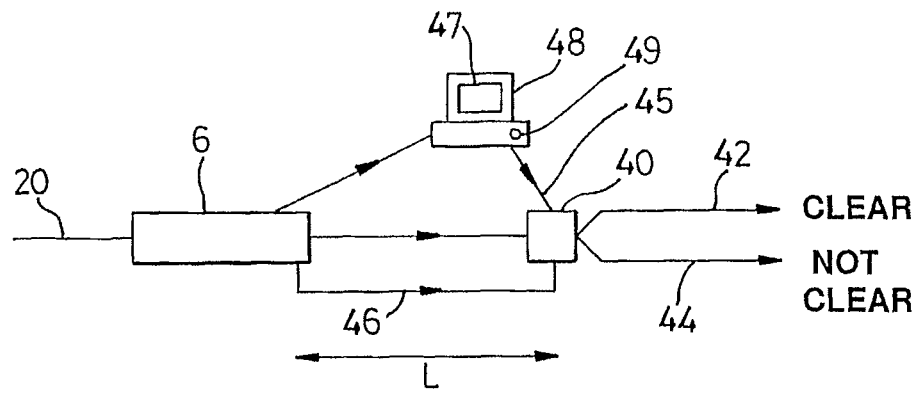
FIG. 6 is a schematic diagram of a baggage sorting system according to an embodiment of the invention including the scanning system of FIG. 1.

Referring to FIG. 6 an in-line real time tomography baggage sorting system comprises the scanning system 6 of FIG. 1 with the conveyor 20 passing through it. Downstream of the scanning system 6 a sorting device 40 is arranged to receive articles of baggage from the conveyor 20 and move them onto either a clear or 'green' channel conveyor 42 or a not clear or 'red' channel conveyor 44. The sorting device 40 is controlled by the automatic sorting output signals via a control line 46 from the processing system 30, which are indicative of the decision of the processing system 30 as to whether the item is clear or not, and also by signals from a workstation 48 to which it is connected via line 45. The images from the scanning system 6 and signals from the processing system 30, indicative of the red and green probabilities and the nominal decision of the processing system 30, are also fed to the workstation 48. The workstation is arranged to display the images on a screen 47 so that they can be viewed by a human operator, and also to provide a display indicative of the green and red probabilities and the nominal automatic sorting decision. The user at the workstation can review the images and the probabilities, and the automatic sorting output, and decide whether to accept or override the decision of the scanning system, if that was to allocate the item to the red or green category, or to input a decision if the scanning system decision was to allocate the item to the 'amber' category. The workstation 48 has a user input 49 that enables the user to send a signal to the sorting device 40 which can be identified by the sorting device as over-riding the decision of the scanning system. If the over-riding signal is received by the sorting device, then the sorting device does over-ride the decision of the scanning system. If no over-ride signal is received, or indeed if a confirming signal is received from the workstation confirming the decision of the scanning system, then the sorting device sorts the item on the basis of the decision of the scanning system. If the sorting system receives an amber' signal from the scanning system relating to an item, then it initially allocates that item to the 'red' category to be put into the red channel. However, if it receives an input signal from the workstation before it sorts the item indicating that it should be in the 'green' category, then it sorts the item to the green channel.

In a modification to the system of FIG. 6, the sorting can be fully automatic, with the processing system giving one of just two sorting outputs, 'clear' and 'not clear', allocating the item to either the green or the red channel. It would also be possible for the processing system to determine just one probability Pr(threat) with one threshold value and allocate the item to one of the two categories depending on whether the probability is above or below the threshold. In this case the allocation would still be provisional and the operator would still have the option of overriding the automatic sorting. In a further modification the automatic category allocation of the scanning system is used as the final allocation, with no user input at all. This provides a fully automated sorting system.

In the system of FIG. 6, the scan speed is matched to the conveyor velocity, so that the baggage can be moved at a constant velocity from a loading area where it is loaded onto the conveyor 20, through the scanning system 6, and on to the sorting device 40. The conveyor 20 extends for a distance L, between the exit of the scanning system 6 and the sorting device 40. During the time that a baggage item takes to travel the distance L on the conveyor 20, an operator can view the image data of the item under inspection, and the initial category allocation determined by the scanning system, and confirm or reject the automated decision of the RTT system. Typically the baggage would then be either accepted into the Clear channel and passed forward ready for transportation or rejected into the Not Cleared channel for further investigation.

In this RTT multi-focus system, the RTT scanning unit 8 is able to operate at full baggage belt speed, and hence no baggage queuing or other divert mechanism is required for optimal system operation. In integrated systems such as this, the limited throughput capability of conventional rotating source systems is a significant constraint. Often this means placing multiple conventional CT machines in parallel, and using sophisticated baggage handling systems to switch the item for inspection to the next available machine. This complexity can be avoided with the arrangement of FIG. 6.

Figure 7:
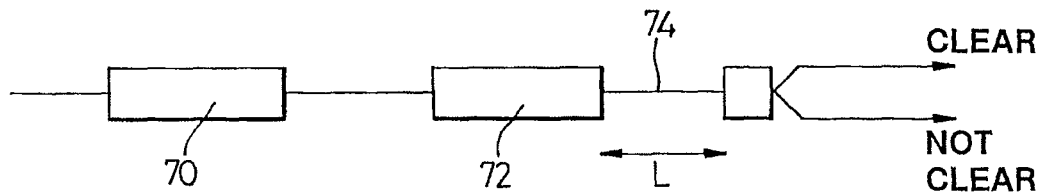
FIG. 7 is a schematic diagram of a baggage sorting system according to a further embodiment of the invention.

Referring to FIG. 7 a second embodiment of the invention comprises a redundant system in which two RTT scanning systems 70, 72 are located in series on the same conveyor 74 such that if one system were to be taken out of service, then the other could continue to scan baggage. In either case, the conveyor belt 74 would continue to run through both scanning systems 70, 72 at standard operating belt speed.

Figure 8A:
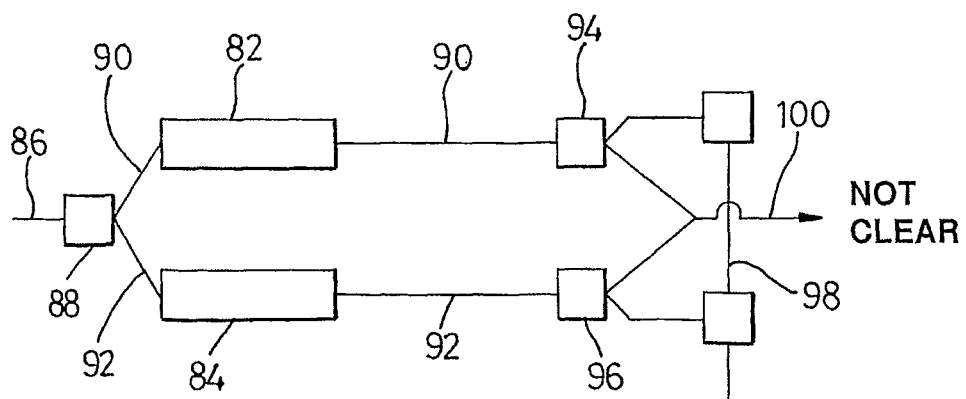
FIG. 8a is a schematic diagram of baggage sorting systems according to further embodiments of the invention.

Referring to FIG. 8a in a third embodiment there is provided a more complex redundant system in which two RTT systems 82, 84 are operated in parallel. A first main incoming conveyor 86 brings all items to be sorted to a first sorting device 88 which can transfer items onto either one of two further conveyors 90, 92. Each of these two conveyors 90, 92 passes through a respective one of the scanning systems 82, 84, which will scan the items and enable a decision to be made as to whether to clear the item or not. A further sorting device 94, 96 is provided on each of the two conveyors 90, 92 which is arranged to sort the baggage onto a common 'green channel' conveyor 98 for onward transportation, or a 'red channel' conveyor 100 if it is not cleared, where it can undergo further investigation. In this configuration, it is possible to run the input conveyor 86, and the 'green channel' conveyor at a higher speed than the RTT conveyor speed, typically up to twice the speed. For example in this case the main incoming conveyor 86 and the common 'green channel' conveyor move at a speed of 1 m/s whereas the scanning conveyors 82, 84 travel at half that speed, i.e. 0.5 m/s. Of course the system can be expanded with more parallel RTT systems, with the ratio of the speed of the main incoming conveyor to that of the scanner conveyors being equal to, or substantially equal to, the number of parallel scanners, although the sorting devices may become unreliable at more than about 1 m/s main conveyor speed.

Figure 8B:
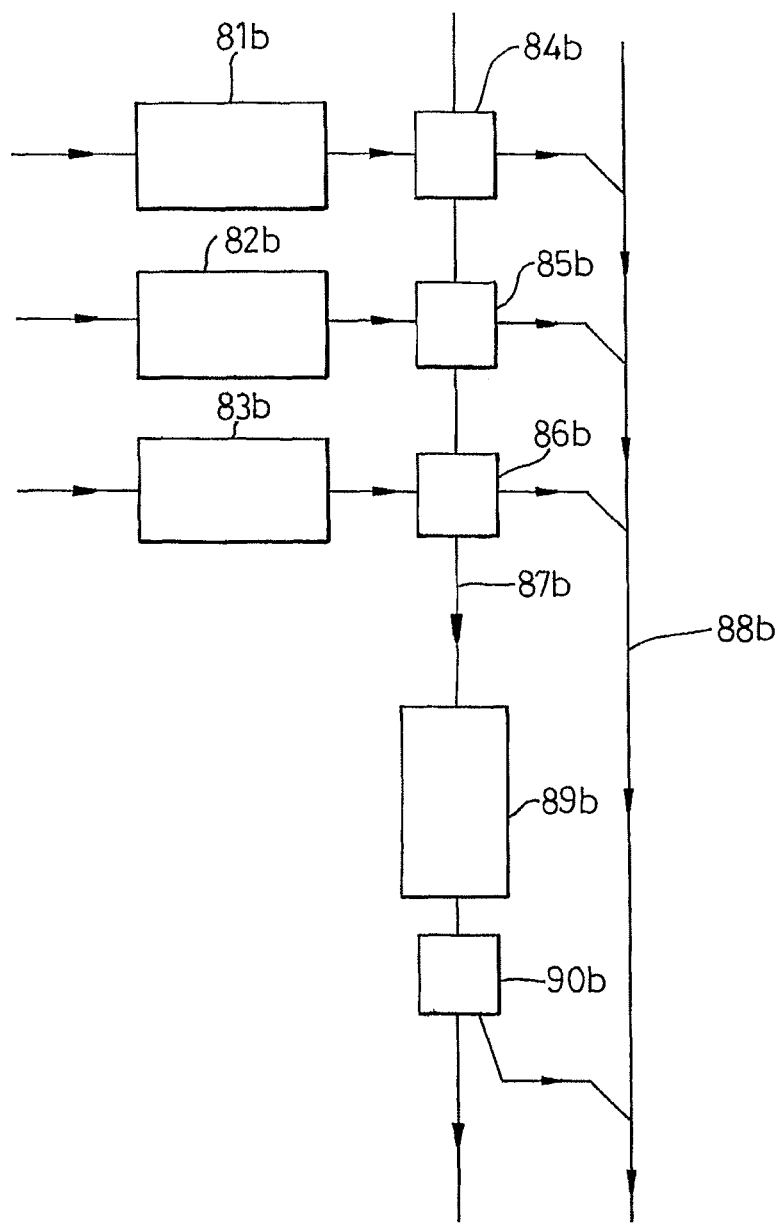
FIG. 8b is another schematic diagram of baggage sorting systems according to further embodiments of the invention.

Referring to FIG. 8b, in a further embodiment a baggage sorting system comprises a number of RTT scanners 81b, 82b, 83b, typically up to about 60 in one system, each associated with a respective check-in desk. A sorting device 84b, 85b, 86b is associated with each RTT scanner, and baggage is conveyed on a conveyor from each RTT scanner to its associated sorting device. Each sorting device 84b, 85b, 86b sorts the baggage, in response to signals from its scanner, onto either a common clear channel conveyor 88b, or a common reject channel conveyor 87b. A further backup RTT scanner 89b is provided on the reject channel conveyor 87b, with an associated sorting device 90b, that can leave baggage on the reject channel conveyor 87b, or transfer it to the clear channel conveyor 88b.

Under normal operation, each of the primary scanners 81b, 82b, 83b sorts the baggage, and the backup or redundant scanner 89b simply provides a further check on items sorted into the reject channel. If that scanner determines that an item of baggage represents no, or a sufficiently low threat, then it transfers it to the clear channel. If one of the primary scanners is not functioning or has a fault, then its associated sorting device is arranged to sort all baggage from that scanner to the reject channel. Then, the back-up scanner 89b scans all of that baggage and controls sorting of it between the clear and reject channels. This enables all the check-in desks to continue to function while the faulty scanner is repaired or replaced.

Figure 8C:
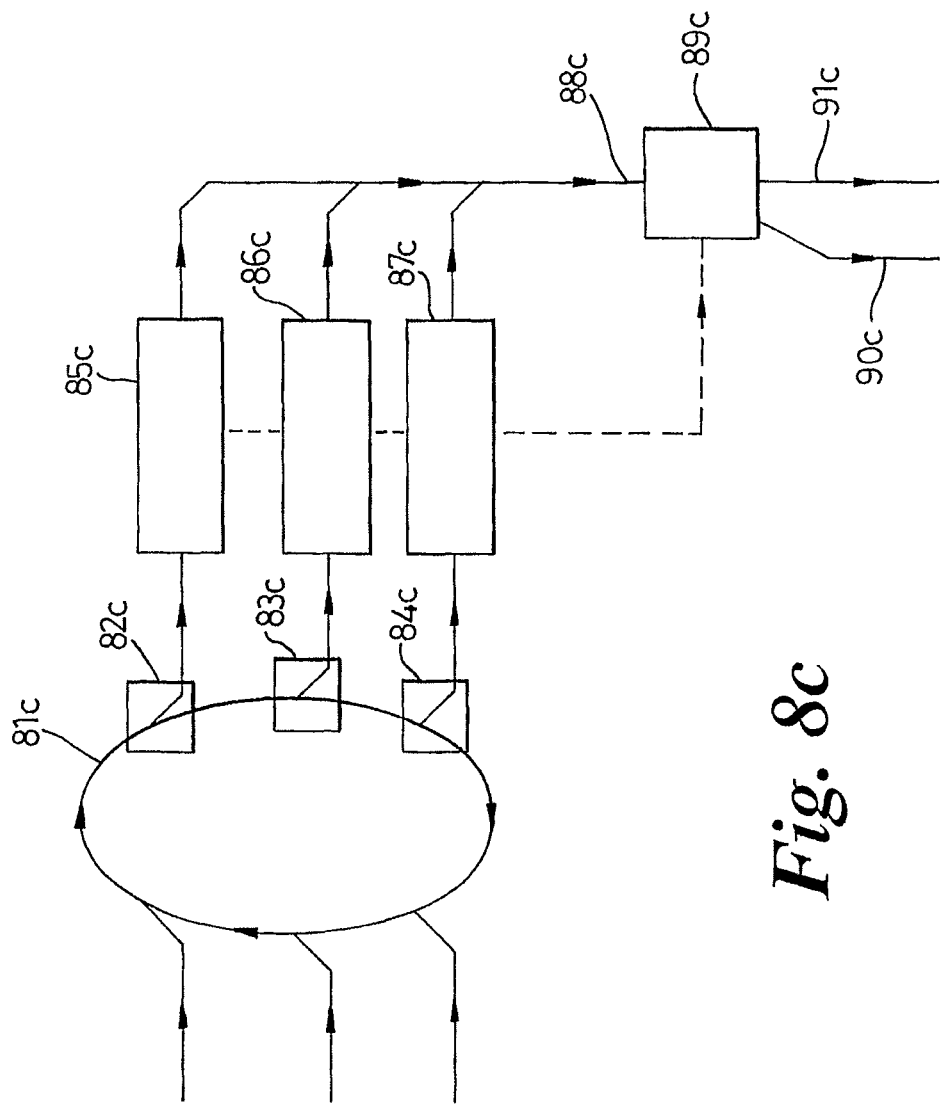
FIG. 8c is another schematic diagram of baggage sorting systems according to further embodiments of the invention.

Referring to FIG. 8c, in a further embodiment, baggage from each of the check-in desks is transferred via a plurality of separate conveyors onto a central loop or carousel 81c, on which it circulates continuously. A number of sorting devices 82c, 83c, 84c are each arranged to transfer items of baggage from the loop 81c to a respective conveyor leading to a respective RTT scanner 85c, 86c, 87c. The sorting devices 82c, 83c, 84c are controlled by the scanners to control the rate at which baggage items are fed to each of the scanners. From the scanners, conveyors transfer all of the baggage items to a common exit conveyor 88c leading to a further sorting device 89c. This is controlled by all of the scanners to sort each of the baggage items between a clear channel 90c and a reject channel 91c.

In order to track the movement of each item of baggage, each item is given a 6-digit ID, and its position on the conveyor recorded when it first enters the system. The scanners can therefore identify which item of baggage is being scanned at any one time, and associate the scanning results with the appropriate item. The sorting devices can therefore also identify the individual baggage items and sort them based on their scanning results. The number of scanners and the speeds of the conveyors in this system are arranged such that, if one of the scanners is not functioning, the remaining scanners can process all of the baggage that is being fed onto the loop 81*c* from the check-in desks.

In a modification to this embodiment, the sorting devices 82*c*, 83*c*, 84*c* that select which items are transferred to each scanner are not controlled by the scanners, but are each arranged to select items from the loop 81*c* so as to feed them to the respective scanner at a predetermined rate.

Figure 9:
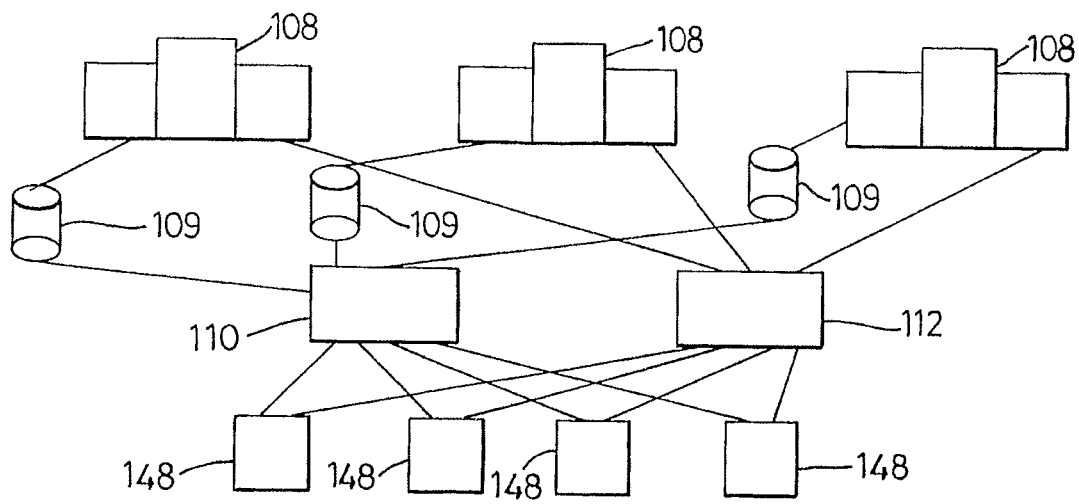
FIG. 9 is a schematic diagram of a networked baggage sorting system according to a further embodiment of the invention.

Referring to FIG. 9 a networked system according to a further embodiment comprises three scanning systems 108 similar to that of FIG. 6, and four operator workstations 148. The video image outputs from the three RTT scanning systems 108 are connected via respective high bandwidth point-to-point video links to real time disk arrays 109 which providing transient storage for the raw image data, to a redundant video switch 110. The disk arrays 109 are in turn connected to each of the workstations 148. The video switch 110 is therefore able to transmit the raw video image output from each of the scanning systems 108 from its temporary storage, to any one of the workstations 148, where it can be used to create 3-dimensional video images which can be viewed off-line. The outputs from the scanning system for the red/green probability signals and the automatic sorting allocation signals are connected to a redundant conventional Ethernet switch 112, which is also connected to each of the workstations. The Ethernet switch is arranged to switch each of the probability signals and the sorting allocation signals to the same workstation 148 as the associated video signal. This allows image data from the multiple machines together with the automatic allocation and probabilities assigned to the allocation, to be switched through to the bank of operator workstations 148 where an operator can both monitor the performance of the baggage inspection system and determine the destination of baggage assigned an amber threat level.

Alternatively, a networked system comprises a single scanning system 108 connected to a server and a workstation 148. The video image output from the scanning system 108 is connected to a real time disk array 109, which provides transient storage for the raw image data. The disk array 109 is in turn connected to the workstation 148. The probability signal and allocation signal outputs are sent to the workstation 148 together with the associated video image output to be monitored by an operator. The networked single scanning system may be part of a networked system with multiple scanning systems.

Figure 10:
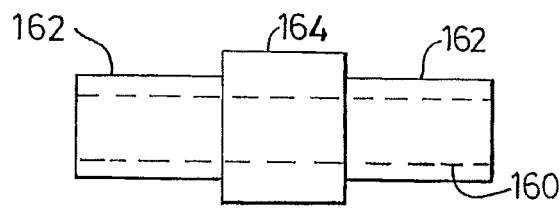
FIG. 10 is a schematic plan view of a stand-alone scanning system according to a further embodiment of the invention.
Figure 11:
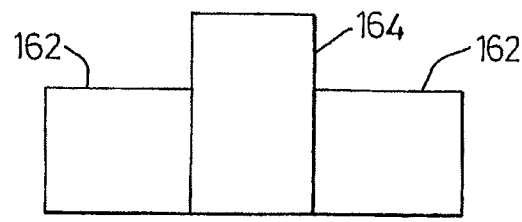
FIG. 11 is a schematic side view of the system of FIG. 10.

Referring to FIGS. 10 and 11, in a further embodiment an in-line scanner has a conveyor belt 160 just as long as the main scatter shields 162. In such standalone system configurations, the item for inspection is placed onto the conveyor belt 160 and the item loaded into the system. The item is then scanned through the scanner machine 164 and images are generated. Often, in conventional systems, the item is pre-screened with a simple transmission X-ray system to identify likely threat areas prior to computed tomography screening of selected planes in the object. Such applications are simple for a real-time multi-focus system to cope with. Here, no pre-screening would be used and a true three-dimensional image of the complete item would be obtained.

In some embodiments the locus of source points in the multi-focus X-ray source will extend in an arc over an angular range of only 180 degrees plus the fan beam angle (typically in the range 40 to 90 degrees). The number of discrete source points is advantageously selected to satisfy the Nyquist sampling theorem. In some embodiments, as in that of FIG. 1, a complete 360 degree ring of source points is used. In this case, the dwell-time per source point is increased over a 180+ fan beam configuration for a given scan rate and this is advantageous in improving reconstructed image signal-to-noise ratio.

Figure 12:
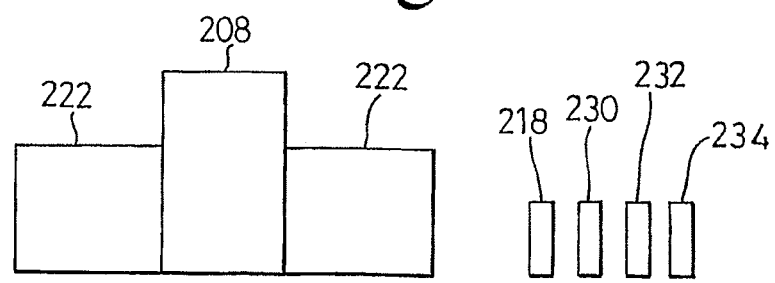
FIG. 12 is a schematic side view of a modular scanning system according to a further embodiment of the invention.

The scanner system of FIG. 1 is an integrated scanner system, in that the control, processing, power supply, and cooling units 18, 30, 32, 34 are housed in a unit with the scanning system 8 and the screening 22. Referring to FIG. 12, in a further embodiment there is provided a modular system in which some, or all, of the control, processing, power supply, and cooling racks 218, 230, 232, 234 are located remotely from the scanning unit 208 comprising multi-focus X-ray source and sensor array. It is advantageous to use a modular design to facilitate easy installation, particularly in baggage handling hall environments, where systems may be suspended from the ceiling or in regions with restricted access. Alternatively, a complete system can be configured as an integrated unit with the sub-assembly units co-located within a single housing.

In some embodiments, including that of FIG. 1, a single X-ray detector ring is used. This is inexpensive to construct and provides adequate signal-to-noise performance even at high image scanning rates with a simple fan-beam image reconstruction algorithm. In other embodiments (particularly for large image reconstruction circle diameter) it is preferable to use a multi-ring sensor array with a plurality of circular or part-circular groups of sensors arranged adjacent to each other, spaced along the axis of the system offset from the source. This enables a more complex cone-beam image reconstruction algorithm to be used in the processing system. The use of a multi-ring sensor increases dwell-time per source point resulting in larger integrated signal size and consequent improvement in signal-to-noise ratio in the reconstructed image.

Central to the design of the embodiments described above, which use a multi-focus X-ray source based computed tomography system, is the relationship between the angular rotational speed of the source and the velocity of the conveyor system passing through the scanner. In the limit that the conveyor is stationary, the thickness of the reconstructed image slice is determined entirely by the size of the X-ray focus and the area of the individual elements of the X-ray detector array. As conveyor speed increases from zero, the object under inspection will pass through the imaging slice during rotation of the X-ray beam and an additional blurring will be introduced into the reconstructed image in the direction of the slice thickness. Ideally, the X-ray source rotation will be fast compared to the conveyor velocity such that blurring in the slice thickness direction will be minimized.

A multi-focus X-ray source based computed tomography system for baggage inspection provides a good ratio of angular source rotational speed to linear conveyor speed for the purposes of high probability detection of threat materials and objects in the item under inspection. As an example, in the embodiment of FIG. 1, the conveyor speed is 0.5 m/s as is common in airport systems. The source can achieve 240 source rotations about the conveyor per second, so the object under inspection will move a distance of 2.08 mm through the imaging slice during the scan. In a conventional system with source rotation of 4 revolutions per second, the object under inspection will move a distance of 62.5 mm through the imaging slice during the scan at the same belt speed.

The primary goal of an inspection system for detection of threat materials is to detect accurately the presence of threat materials and to pass as not suspect all other materials. The larger the blurring in the slice direction that is caused by conveyor motion during a scan, the greater the partial volume artifact in the reconstructed image pixel and the less accurate the reconstructed image density. The poorer the accuracy in the reconstructed image density, the more susceptible the system is to provide an alarm on non-threat materials and to not raise an alarm on true threat materials. Therefore, a real-time tomography (RTT) system based on multi-focus X-ray source technology can provide considerably enhanced threat detection capability at fast conveyor speeds than conventional mechanically rotated X-ray systems.

Due to the use of an extended arcuate anode in a multi-focus X-ray source, it is possible to switch the electron source such that it jumps about the full length of the anode rather than scanning sequentially to emulate the mechanical rotation observed in conventional computed tomography systems. Advantageously, the X-ray focus will be switched to maximize the distance of the current anode irradiation position from all previous irradiation positions in order to minimize the instantaneous thermal load on the anode. Such instantaneous spreading of the X-ray emission point is advantageous in minimizing partial volume effect due to conveyor movement so further improving reconstructed pixel accuracy.

The high temporal resolution of RTT systems allows a high level of accuracy to be achieved in automated threat detection. With this high level of accuracy, RTT systems can be operated in unattended mode, producing a simple two-state output indication, with one state corresponding to a green or clear allocation and the other to a red or not clear allocation. Green bags are cleared for onward transport. Red bags represent a high level of threat and should be reconciled with the passenger and the passenger barred from traveling.

Further embodiments of the invention will now be described in which data relating to the scattering of X-rays as well as that relating to transmitted X-rays is recorded and used to analyze the scanned baggage items.

Figure 13:
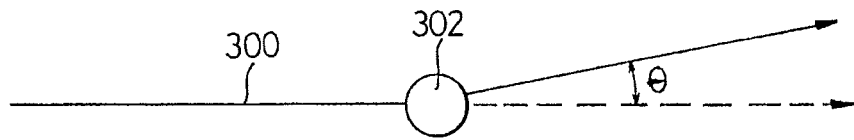
FIG. 13 is a diagram of an X-ray scattering event.

Referring to FIG. 13 when a beam 300 of X-rays passes through an object 302, some of the X-rays are transmitted straight through it, and exit the object traveling in the same direction as they entered it. Some of the X-rays are scattered through a scattering angle θ, which is the difference between the direction in which they enter the object and the direction in which they leave it. As is well known there are two types of scattering that occur: coherent or Bragg scattering, which is concentrated around scattering angles of 5 degrees, typically in the range 4 degrees to 6 degrees, and incoherent or Compton scattering in which the X-ray is scattered through larger angles. Bragg scattering increases linearly with the atomic number of the object and obeys the formula:

$$n\lambda = 2d \sin \theta$$

where n is an integer, λ is the wavelength of the X-ray, and d is the inter-atomic distance in the object.

Therefore the amount of Bragg scattering gives information about the atomic structure of the object. However, it does not vary smoothly with atomic number.

The amount of Compton scattering is dependent on, and varies smoothly with, the electron density of the object, and therefore the amount of scattering at higher scatter angles gives information about the electron density of the object, and hence about its atomic number.

Figure 14:
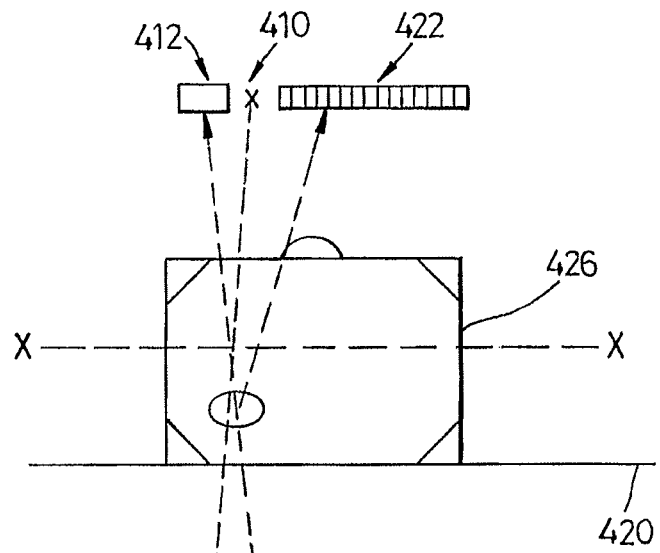
FIG. 14 is a longitudinal section through a security scanning system according to a further embodiment of the invention.

Referring to FIG. 14 a security scanning system according to a further embodiment of the invention comprises a multi-focus X-ray source 410 which is the same as that of FIG. 1, and a circular detector array 412 and conveyor 420 that are also the same as those of FIG. 1. However, in this embodiment, the system comprises a further cylindrical array of detectors 422 which also extends around the conveyor at the same radius as the circular detector array 412 but on the other side axially of the source 410. Whereas the circular detector array is arranged to detect X-rays transmitted through the object 426, the cylindrical detector array 422 is arranged to detect X-rays scattered in the object. The scatter detector array 422 is made up of a number of circular arrays or rings 422a, 422b of detectors, and the detectors in each ring are equally spaced around the conveyor so that they are arranged in a number of straight rows extending in the axial direction of the scanner.

The detectors in the scatter detector array 422 are energy resolving detectors such that individual X-ray interactions with each detector produce a detector output that is indicative of the energy of the X-ray. Such detectors can be fabricated from wide bandgap III-V or II-IV semiconductor materials such as GaAs, HgI, CdZnTe or CdTe, a narrow gap semiconductor such as Ge, or a composite scintillation detector such as NaI(Ti) with photomultiplier tube readout.

Figure 15:
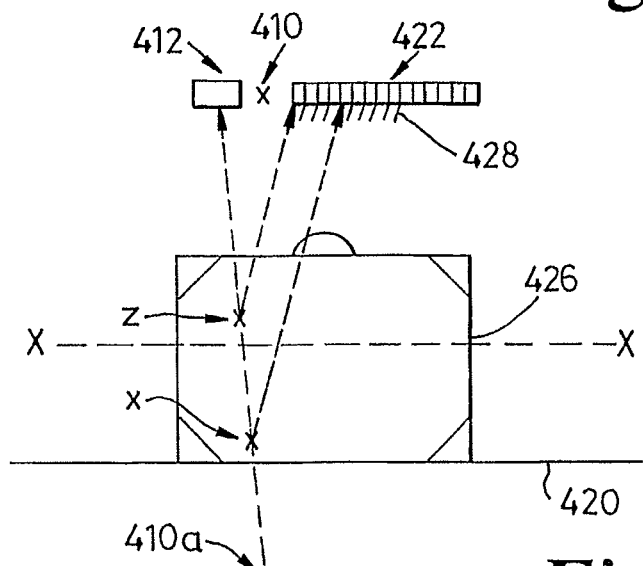
FIG. 15 is a further longitudinal section through the system of FIG. 14 showing how different scatter events are detected.
Figure 16:
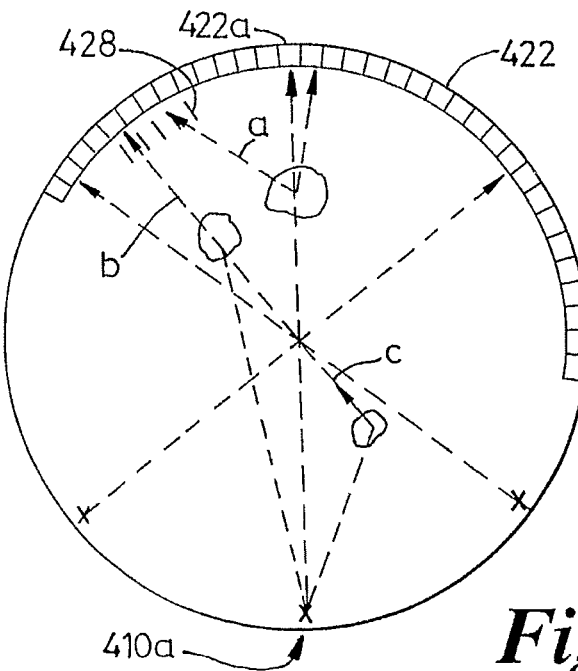
FIG. 16 is a transverse section through the system of FIG. 14.

Referring to FIG. 15, a collimator 428 is provided in front of the scattering detectors 422. The collimator 428 provides a barrier that prevents X-rays from reaching each detector unless it comes from a particular receiving direction. For each detector in the array 422, the receiving direction passes through the central longitudinal axis X-X of the scanner, as can be seen in FIG. 16. However, the receiving direction is not perpendicular to the axis X-X, but is inclined at about 5.degree. to the plane of the detector rings 422a, 422b in the direction towards the source 410, as can be seen in FIG. 15.

Referring to FIG. 15 it will be appreciated that X-rays incident on any one of the detectors of the array 422 must have been scattered from a respective small sub-volume within the thin imaged volume that lies both in the path of the X-ray beam and in the line of the receiving direction from the detector 422. For any coherently scattered X-rays, the axial position of the detector that detects it will be determined by the distance from the active X-ray source point at which the scattering occurred. Detectors nearest the source 410 in the axial direction will detect X-rays scattered furthest from the active X-ray source point. For example X-rays scattered from the point x, which is nearest the active X-ray source point 410a, will be detected by a detector further from the source 410 than X-rays scattered from the point z which is further from the active X-ray source point. Therefore, at any one time, when the active X-ray source point can be identified, the axial position of the detector which detects the scattered X-ray can be used to determine the position of the scattering along the X-ray beam direction.

It will also be appreciated from FIG. 15 that, for this system to work, it is important that the X-ray beam should be narrowly focused in the axial direction of the scanner. Spreading of the beam in the transverse direction, e.g. use of a fan beam spread in the transverse direction will still allow this positioning of coherent scattering events.

Referring to FIG. 16, because the collimator 428 is directed towards the axis of the scanner, X-rays from an active source point 410a that undergo coherent scattering will only be detected by the row of detectors 422a that is on the opposite side of the scanner axis to the active source point, and possibly one or more of the rows close to it on either side depending on how narrowly focused the collimator is. If X-rays are confined to a straight narrow 'pencil' beam, then any X-rays that are scattered incoherently through larger angles will not be detected at all as they will be cut off by the collimator 428. An example of such an X-ray is shown by arrow 'a' in FIG. 16. However, if a fan beam of X-rays is produced from the active source point

410a, that is spread out through the imaging volume slice in the direction perpendicular to the scanner axis, then X-rays directed further away from the scanner axis can undergo incoherent scattering and reach detectors to either side of the row 422a opposite the active source point. Examples of such X-rays are shown by the arrows b and c. It will be noted that, to reach any detector 422b, the scattering event must take place in the plane passing through the scanner axis and that detector 422b. This means that, for a given active source point and a particular detector, the position of the scattering event of a detected X-ray can be identified as being in the plane passing through the scanner axis and that detector. If the exact position of the scattering event is to be determined then other information is needed. For example if information regarding the position of objects within the imaging volume is available, for example from tomographic imaging data, then the scattering can be associated with the most likely object as will be described in more detail below.

From the Bragg scattering data, for each detected scattering event, the combination of the X-ray energy and the scatter angle can be used to determine the inter-atomic distance d of the material in which the scattering event took place. In practice, the scatter angle can be assumed to be constant, and the energy used to distinguish between different materials. For the Compton scattering, the level of scattering from each volume of the scanning volume gives an indication of the density of the material in that volume. The ratio of Compton to coherent scatter can also be determined and used as a further parameter to characterize the material of the imaged object.

Due to the short dwell time for each X-ray source point, the number of detected scattered X-rays for each source point will always be very low, typically less than five. In order to form a reasonable coherent scatter signal it is necessary to collect scatter data for all source points within a tomographic scan and then accumulate the results for each sub-volume of the imaging volume. For a scanner with 500 source points, and an average of one coherent diffraction scatter result per sub-volume per scan, then following accumulation of the set of data, each sub-volume will have 500 results associated with it, corresponding to 500 scattering events within that sub-volume. A typical sub-volume occupies an area within the imaging plane of a few square centimeters, with a volume thickness of a few millimeters.

Figure 17:
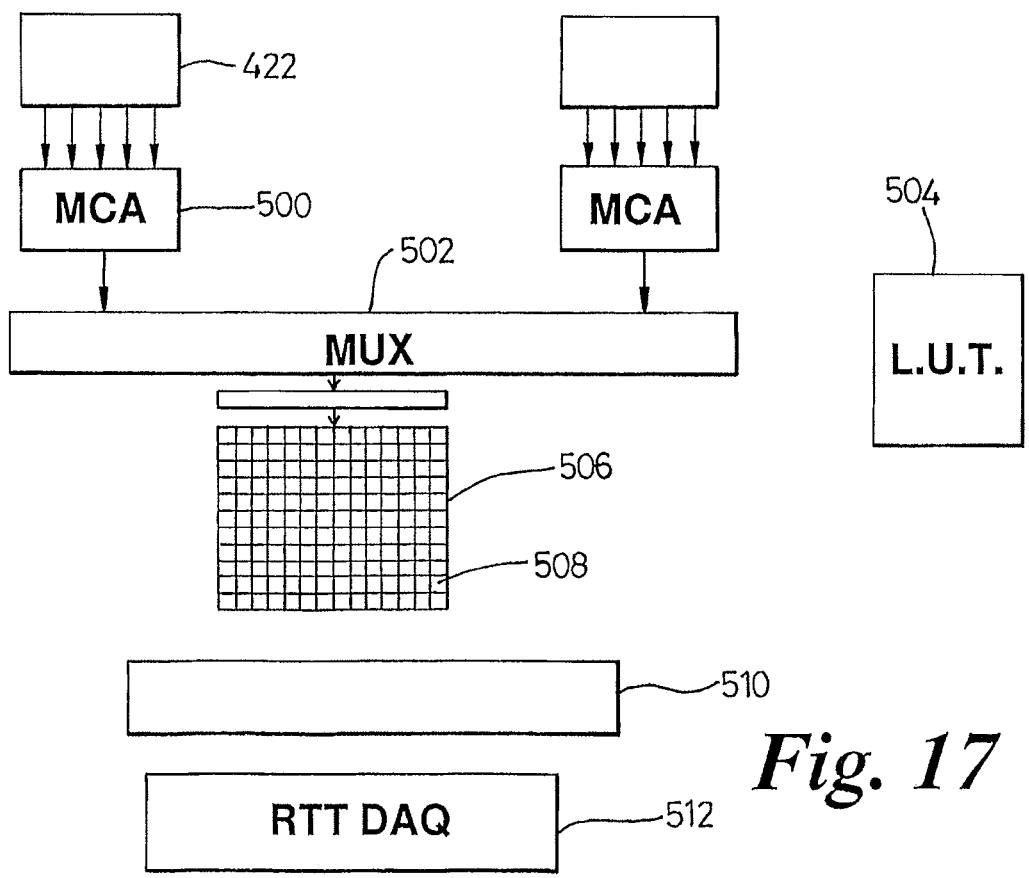
FIG. 17 is a schematic diagram of a data acquisition system of the scanning system of FIG. 14.

Referring to FIG. 17, the data acquisition system arranged to accumulate data from the scatter detector array 422 of the scanner of FIGS. 14 to 16 comprises a multi-channel analyzer 500 associated with each of the detectors 422. Each MCA 500 is arranged to receive the output signals from the detector, and allocate each X-ray detected to one of a number of X-ray energy ranges or channels, and output a signal indicative of the energy range in which the detected X-ray falls. A multiplexer 502 is arranged to receive the outputs from each of the MCAs 500. A look-up table 504 is also provided which has entries in it that, for a given source point and detector, identify the sub-volume within the imaging volume in which the X-ray was scattered. The system further comprises an image memory 506 which includes a number of memory areas 508, each of which is associated with a respective sub-volume within the scanner imaging plane.

Data is loaded into each memory area 508 automatically by the multiplexer 502 under the direction of the look up table 504. The look up table is loaded with coefficients prior to scanning that map each combination of detector 422 and MCA 500 to a respective image location 508, one look up table entry per X-ray source position. Those pixels, i.e. detectors 422, that are in the forward direction, i.e. substantially in the direction that the photon is traveling from the source prior to any interaction, are assumed to record coherent scatter photons at small beam angles of about 4-6 degrees. Those pixels 422 that are not in the forward direction are assumed to record incoherent scattered photons due to the Compton scattering effect. Hence, the image memory 506 is actually "three dimensional"—two dimensions represent location in the image while the third dimension holds scattered energy spectra for both coherent (lo 8-bits) and incoherent scattering (hi 8 bits). The look up table 504 will also instruct the multiplexer 502 as to the type of data that is being collected for each MCA 500 at each projection so that the appropriate memory space is filled.

Once the scatter data has been collected for a given scan, the data is transferred to and synchronized, by a projection sequencer 510, with the main RTT data acquisition system 512, which is described above with reference to FIG. 4. Hence the reconstructed image data and scatter data are passed through simultaneously to the threat detection system, which can use it to determine suitable parameters for analysis.

For each scan, the tomographic image data from the transmission detectors 412 produces data relating to the X-ray attenuation for each pixel of the image, which in turn corresponds to a respective sub-volume of the tomographic imaging volume. This is obtained as described above with reference to FIG. 4. The data from the scatter detectors 422 provides, as described above, data relating to the amount of coherent scattering within each sub-volume, and data relating to the amount of incoherent scattering within each sub-volume. This data can therefore be analyzed in a threat detection processor similar to that of FIG. 5. In this case the parameters of the data which are extracted can relate to the image data or the scatter data or combinations of two or more types of data. Examples of parameters that are extracted from the data are the ratio of coherent to incoherent scatter, material types as determined from coherent scatter data, material density as determined from incoherent scatter data, correlation of CT image pixel values with scatter data. Also parameters for the scatter data corresponding to those described above for the transmission data can also be determined.

Referring to FIG. 18, in a further embodiment of the invention the transmission detectors 512 that are used to generate the tomographic image data are arranged to measure the X-ray transmission over different energy ranges. This is achieved by having two sets of detectors 512a, 512b, each forming a ring around the conveyor. The two sets are at different axial locations along the direction of travel of the conveyor, in this case being adjacent to each other in the axial direction. The first set 512a has no filter in front of it, but the second set 512b has a metal filter 513 placed between it and the X-ray source 510. The first set of detectors 512a therefore detects transmitted X-rays over a broad energy range, and the second set 512b detects X-rays only in a narrower part of that range at the high energy end.

As the item to be scanned moves along the conveyor, each thin volume or slice of it can be scanned once using the first set of detectors 512a and then scanned again using the second set 512b. In the embodiment shown, the same source 510 is used to scan two adjacent volumes simultaneously, with data for each of them being collected by a respective one of the detector sets 512a, 512b. After a volume of the item has moved past both sets of detectors and scanned twice, two sets of image data can be formed using the two different X-ray energy ranges, each image including transmission (and hence attenuation) data for each pixel of the image. The two sets of image data can be combined by subtracting that for the second detector set 512*a* from that of the first 512*b*, resulting in corresponding image data for the low energy X-ray component.

The X-ray transmission data for each individual energy range, and the difference between the data for two different ranges, such as the high energy and low energy, can be recorded for each pixel of the image. The data can then be used to improve the accuracy of the CT images. It can also be used as a further parameter in the threat detection algorithm.

It will be appreciated that other methods can be used to obtain transmission data for different ranges of X-ray energies. In a modification to the system of FIGS. 18 and 19, balanced filters can be used on the two detector sets. The filters are selected such that there is a narrow window of energies that is passed by both of them. The image data for the two sets of detectors can then be combined to obtain transmission data for the narrow energy window. This enables chemical specific imaging to be obtained. For example it is possible to create bone specific images by using filters balanced around the calcium K-edge energy. Clearly this chemical specific data can be used effectively in a threat detection algorithm.

In a further embodiment, rather than using separate filters, two sets of detectors are used that are sensitive to different energy X-rays. In this case stacked detectors are used, comprising a thin front detector that is sensitive to low energy X-rays but allows higher energy X-rays to pass through it, and a thick back detector sensitive to the high energy X-rays that pass through the front detector. Again the attenuation data for the different energy ranges can be used to provide energy specific image data.

In a further embodiment two scans are taken of each slice of the object with two different X-ray beam energies, achieved by using different tube voltages in the X-ray source, for example 160 kV and 100 kV. The different energies result in X-ray energy spectra that are shifted relative to each other. As the spectra are relatively flat over part of the energy range, the spectra will be similar over much of the range. However, part of the spectrum will change significantly. Therefore comparing images for the two tube voltages can be used to identify parts of the object where the attenuation changes significantly between the two images. This therefore identifies areas of the image that have high attenuation in the narrow part of the spectrum that changes between the images. This is therefore an alternative way of obtaining energy specific attenuation data for each of the sub-volumes within the scanned volume.

Referring to FIG. 20 in a further embodiment of the invention, two different X-ray energy spectra are produced by providing an anode 600 in the X-ray tube that has target areas 602, 604 of two different materials. In this case, for example, the anode comprises a copper base 606 with one target area 602 of tungsten and one 604 of uranium. The electron source 610 has a number of source points 612 that can be activated individually. A pair of electrodes 612, 614 is provided on opposite sides of the path of the electron beam 616 which can be controlled to switch an electric field on and off to control the path of the electron beam so that it strikes either one or the other of the target areas 602, 604. The energy spectrum of the X-rays produced at the anode will vary depending on which of the target areas is struck by the electron beam 616.

This embodiment uses an X-ray source similar to that of FIG. 1*a*, with the different target areas formed as parallel strips extending along the anode 27. For each active electron source point two different X-ray spectra can be produced depending on which target material is used. The source can be arranged to switch between the two target areas for each electron source point while it is active. Alternatively the scan along the anode 27 can be performed twice, once for one target material and once for the other. In either case further electron beam focusing wires may be needed to ensure that only one or the other of the target materials is irradiated by the electron beam at one time.

Depending on the angle at which the X-ray beam is extracted from the anode, the beams from the two target areas 602, 604 can in some cases be arranged to pass though the same imaging volume and be detected by a common detector array. Alternatively they may be arranged to pass through adjacent slices of the imaging volume and detected by separate detector arrays. In this case the parts of the imaged item can be scanned twice as the item passes along the conveyor in a similar manner to the arrangement of FIG. 18.

Referring to FIG. 21, in a further embodiment, two detector arrays are provided in a single scanner, adjacent to each other in the axial direction, one 710 corresponding to that of FIG. 1 and being arranged to form a RTT image, and the other, 712, being of a higher resolution, and being arranged to produce a high resolution projection image of the scanned object. In this embodiment the high resolution detector array 712 comprises two parallel linear arrays 714, 716 each arranged to detect X-rays at a different energy, so that a dual energy projection image can be produced. In the embodiment of FIG. 22, the high resolution array 812 comprises two stacked arrays, a thin array on top arranged to detect lower energy X-rays but transparent to higher energy X-rays, and a thicker array beneath arranged to detect higher energy X-rays. In both cases, the two detector arrays are arranged close enough together in the axial direction to be able to detect X-rays from a single linear array of source points.

Figure 23:
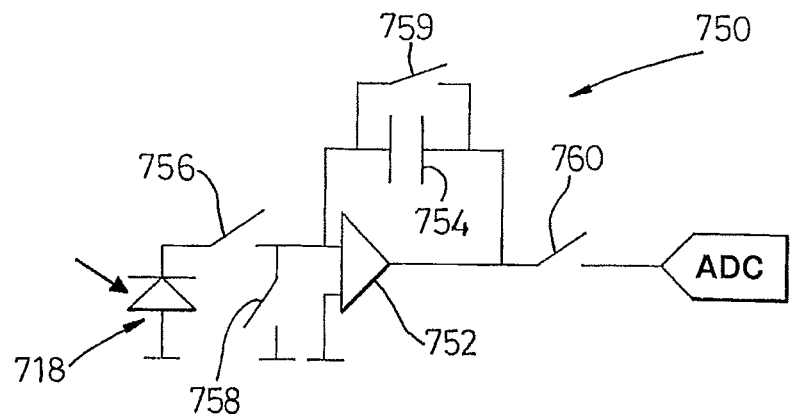
FIG. 23 is a circuit diagram of a data acquisition circuit of the embodiment of FIG. 21.

In order to provide a projection image, data needs to be captured from all of the detectors in the high resolution array 712, 812 when only one source point is active. Referring to FIG. 23, in order to do this each detector 718, 818 in the high resolution array is connected to an integrator 750. The integrator comprises an amplifier 752 in parallel with a capacitor 754. An input switch 756 is provided between the detector 718 and the amplifier 752, a reset switch 758 is provided across the input terminals of the amplifier, and a further reset switch 759 connected across the capacitor 754, and a multiplexing switch 760 is provided between the integrator and an analogue to digital converter ADC.

In operation, while the detector 718 is not required to be active, all of the switches except for the multiplexing switch 760 are closed. This ensures that the capacitor 754 is uncharged and remains so. Then, at the start of the period when the detector is required to gather data, the two reset switches 758, 759 are closed so that any X-rays detected by the detector 718 will cause an increase in the charge on the capacitor 754, which results in integration of the signal from the detector 718. When the period for data collection has ended, the input switch 756 is opened, so that the capacitor will remain charged. Then, in order for the integrated signal to be read from the integrator, the output switch 760 is closed to connect the integrator to the ADC. This provides an analogue signal to the ADC determined by the level of charge on the capacitor 754, and therefore indicative of the number of X-rays that have been detected by the detector 718 during the period for which it was connected to the integrator. The ADC then converts this analogue signal to a digital signal for input to the data acquisition system. To produce a single projection image, all of the high resolution detectors are used to collect data at the same time, when one of the X-ray source points is active.

Figure 24:
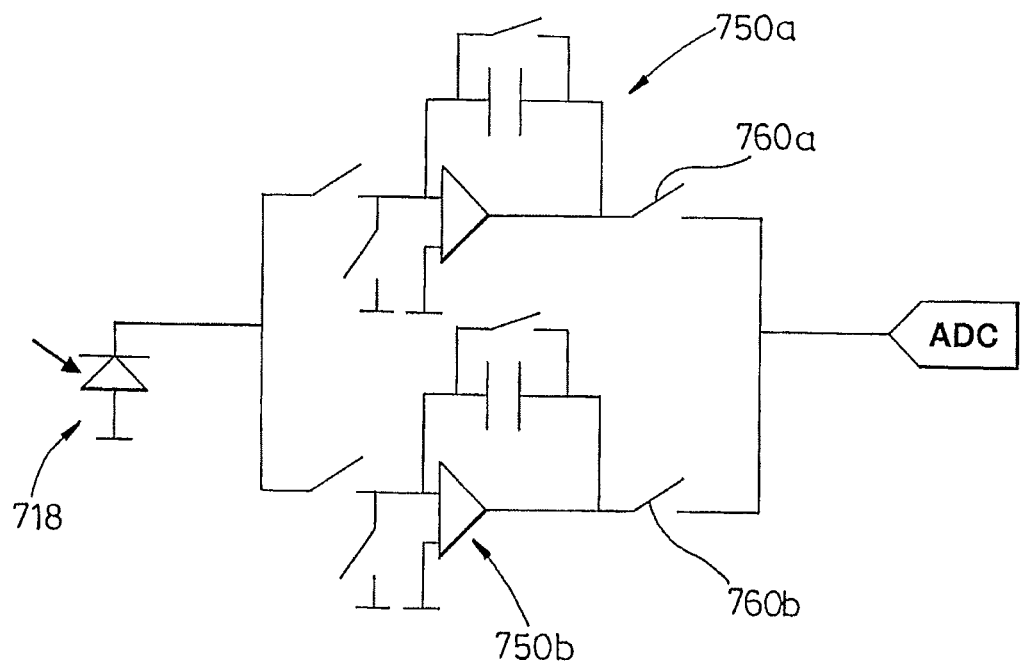
FIG. 24 is a circuit diagram of a data acquisition circuit of a further embodiment of the invention.

Referring to FIG. 24, in a further embodiment, each detector 718 is connected to two integrators 750*a*, 750*b* in parallel, each of which is identical to that of FIG. 23. The outputs from the two integrators are connected via their output switches 760*a*, 760*b* to an ADC. This enables each integrator to be arranged to integrate the signal from the detector 718 at a different point in the scan of the X-ray source, and therefore to collect data for a separate image, the two images being from different angles with different X-ray source points. For example this can be used to produce projection images from orthogonal directions which can be used to build up a high resolution 3-dimensional image, from which the position of features in the imaged package can be determined in three dimensions.

The high resolution image can be useful when combined with the RTT image, as it can help identify items for which higher resolution is needed, such as fine wires.

Liquids Detection

In a particular embodiment of the invention, the threat detection processor, which executes programmatic instructions that process input image data 62 and code the decision trees 64 and parameter extractions 63 shown in FIG. 5, is tuned for the detection of liquids. In an embodiment, a three-dimensional segmentation calculation is used for performing liquid detection. Variations of segmentation calculations, commonly known to persons of ordinary skill in the art and based around a surface detector (for example using a dilate-erode algorithm in all three dimensions) and a volume filling algorithm that grows out from the detected surface, can be implemented. In another embodiment, a volume filling algorithm from a seed point which extends out until a surface is reached is used. In an exemplary embodiment, the surface is determined by analyzing each new pixel in terms of its probability of being part of the volume or otherwise. A pixel value within, for example, one sigma of the mean value of the volume may be considered to be part of the volume while a pixel lying more than two sigma from the mean value may be considered to be not part of the volume. Seed points may be determined by analyzing the image to find regions of similar pixel density and placing a seed point at the centroid location of each such region. In various embodiments, a suitable method is determined based on the statistical properties of the image, the type and severity of image reconstruction artefacts in the image and the intrinsic spatial resolution of the image.

Referring to FIG. 5, a first parameter extraction block 63 is configured to process the input image data 62 to identify a) an object under inspection, b) the outer envelope defining the object under inspection, and c) any flat surfaces within the outer envelope of the object under inspection which lie parallel to the surface of the conveyor in the horizontal plane. Such parallel surfaces can be reliably used to uniquely identify the existence of a liquid contained within a vessel. Next, a second parameter extraction block is configured to locate a contiguous volume of material of uniform density that extends from each such parallel surface element in a vertical direction downwards towards the surface of the conveyor. This method uses a simplified version of the segmentation methods outlined above since the only direction of importance here is in the vertical plane rather than vertical and horizontal planes.

The information obtained by the parameter extraction blocks is passed from the parameter extraction blocks 63 to an associated decision tree 64, where the actual volume of the contiguous volume is calculated and assigned a fit to a predetermined shape matching one or more of oval bottle, rectangular bottle and triangular bottle. The mean reconstructed intensity of the contiguous volume is calculated and this information (volume, shape, density) is passed to the database searcher 65.

Here, the information is compared against a database of known benign materials and known threat materials. For example, a 1.5 liter bottle of sugar laden beverage will have a common exterior dimension of approximately 400 mm (L)×100 mm (diameter) within a thin plastic container with a neck drawing in to a cap and a base with rounded or moulded features. The density of such beverages is typically just greater that that of water and the volume of the liquid will be no greater than 1.5 liters within a container of volume just greater than 1.5 liters. In contrast, an alcoholic beverage is more often in a glass bottle with thicker wall thickness with smaller volume such as 750 ml (bottle of wine) or 330 ml (spirit). Alcohol based bottles will generally be full (i.e. volume of liquid is close to volume of container) and will include characteristic features such as a cork or screw top. Density of the liquid will also be in well known bands. Known threat materials tend to have density just below that of water and so stand out quite clearly. In the case that a clear match is made against a benign material, then no further action is taken. In the case that a threat material is detected, an alarm shall be raised on the operator workstation and the threat object highlighted for further inspection. In one embodiment, density calculations are obtained and then compared, by the processor, against liquid densities stored in a database.

Using a high resolution three dimensional image, such as is obtained using the system of the present invention, allows a very accurate estimate of liquid volume to be made which helps substantially in separating a full vessel from a partially filled bottle. It is noted that virtually all liquids are sold in standard sized quantities (e.g. 1500 ml, 1000 ml, 750 ml, 500 ml, 330 ml, 250 ml) with a high level of filling accuracy. Thus, volume estimation can play a key role in detecting vessels which have been tampered with. The high speed of transit of the object through the data acquisition system of the present invention causes the liquid to have "waves" on its surface. The high speed of data acquisition enables reconstruction of the shape of these waves which are themselves characteristic of the viscosity of the fluid within the container. This additional information is then used to enable differentiation in detection of one liquid from another.

It shall be evident to one skilled in the art that the architecture described here is capable of being implemented in a parallel architecture and that therefore multiple algorithms can be constructed, each looking for either the same type of feature or quite different types of feature (such as liquids and narcotics) at the same time.

Narcotics

In a particular embodiment of the invention, the threat detection processor, which executes programmatic instructions that process input image data 62 and code the decision trees 64 and parameter extractions 63 shown in FIG. 5, is tuned for the detection of narcotics.

In an embodiment, the threat detection processor is tuned by selecting algorithms used in the parameter extraction blocks and by weighting of the results from the parameter extraction blocks 63 as they propagate through the decision trees 64. In an embodiment, the tuning information is stored in the form of parameters which can be updated easily without having to re-program the underlying algorithms and methods.

For detection of narcotics, a first parameter block 63 is tuned to process the input image data 62 to look for contiguous volumes of low density material in both sheet and bulk shapes. In an exemplary embodiment, volumes in the range 1 g/cm3 to 3 g/cm3 are identified. A second parameter block processes these same volumes to determine basic statistical properties of the contiguous volumes to include mean value, standard deviation and skew. A third parameter block searches for collections of randomly oriented parts of small volume which may be determined to be pharmaceuticals. Such randomly oriented particles include tablets in a jar or bag while a structured arrangement of tablets may be observed in pop-out packaging materials. All of this data (volume, shape and statistical properties) is passed to the decision tree which correlates the data from the multiple parameter blocks.

The data is then passed to the database searcher 65 where the data is compared against values stored in a database of known threat materials. It is recognised that raw narcotics, such a heroin or cocaine in powder form, tend to be packaged in relatively ordered shapes with very thin, generally polythene, wrapping. Thus, a package of volume 5 cm3 upwards to 100 cm3 with almost undetectable wrapping with density in the range 1 g/cm3 to 3 g/cm3 is likely to be a suspect bulk narcotic material. Where a close match is determined, an alarm shall be raised on the operator workstation and the threat items highlighted for further inspection.

Currency

In a particular embodiment of the invention, the threat detection processor, which executes programmatic instructions that process input image data 62 and code the decision trees 64 and parameter extractions 63 shown in FIG. 5, is tuned for the detection of currency .It shall be evident to a person skilled in the art that a parallel algorithm architecture may be implemented which allows simultaneous detection of currency and other potential threat items.

Here a first parameter block 63 is tuned to look for "bow-tie" shaped features in the object under inspection. Bundles of currency are typically bound towards their centre, such that the centre of a bundle is marginally thinner than the ends. A second parameter block is tuned to search for rectangular shapes in multiples of the physical dimension of common denominations of currency. A third parameter block is tuned to look for repeating patterns in the blocks found by the first two parameter blocks. These patterns are characteristic of the stacks of individual bundles that tend to be used to make up a collection of currency. A fourth parameter block is tuned to generate statistical properties of the bundles identified by the other three parameter blocks. As an example, a stack of US dollar bills will have a well defined area (approx 150 mm×65 mm) with a thickness which is dependent on the amount of currency involved. The thicker the stack, the less the bow-tie effect. However, each type of currency has certain security features embedded into it (such as a metal strip) or a variation in material type or printing density. This arrangement of subtle information is amplified when many notes are stacked together and can be registered by a repeating block algorithm. This collection of information is passed to the decision tree 64 which correlates the information from the currency specific parameter blocks with the data from all the other parameter blocks and the complete setoff data is passed to the database searcher 65. When a clear match is found between an item in the cargo under inspection and a know type of currency, an alarm is raised on the operator workstation and the relevant currency is highlighted for further inspection.

Tobacco

In a particular embodiment of the invention, the threat detection processor, which executes programmatic instructions that process input image data 62 and code the decision trees 64 and parameter extractions 63 shown in FIG. 5, is tuned for the detection of tobacco, and cigarettes in particular. Cigarettes are characterized by a very repeatable structure which is first determined by the length and diameter of individual cigarettes. Secondly, groups of 10 and/or 20 cigarettes are packed together into a box of known and repeatable size. Thirdly, groups of boxes of cigarettes are packed into arrays of dozens of boxes which occupy a significant volume. Therefore, a first parameter block 63 is tuned to look for repeating array structures with a length and width dimension consistent with known dimensions of cigarettes. A second parameter block is tuned to detect rectangular volumes of predefined aspect ratio matching that of common cigarette packaging with a density that is consistent with typical brands of cigarettes. The results from these two parameter blocks are passed through to a decision tree which correlates the data with other known data from the object under inspection.

If, an exemplary brand of cigarette has an overall length of 90 mm with a filter length of 15 mm and a diameter of 8 mm, a pack of 20 cigarettes will therefore have an external dimension of 92 mm (L)×82 mm (W)×22 m (D). This constitutes, at least in part, the regular repeating structure which is stacked into a larger overall volume. A stack of 48 packets arranged in a 6×8 configuration will have an overall dimension of 132 mm (H)×656 mm (W)×92 mm (D). Within thus structure will be a set of rectangular planes which are established by the higher density cardboard boxes and it is all of this information which is picked up by the automated detection algorithm This information is then passed to a database search which compares the information with known tobacco products. When a clear match is found between an item in the cargo under inspection and a known type of tobacco, and alarm is raised on the operator workstation and the relevant tobacco product is highlighted for inspection. As would be apparent to a person skilled in the art, similar algorithms may be implemented for the detection of cigars and related products.

Nuclear Materials

In a particular embodiment of the invention, the threat detection processor, which executes programmatic instructions that process input image data 62 and code the decision trees 64 and parameter extractions 63 shown in FIG. 5, is tuned for the detection of special nuclear materials, such as Uranium and Plutonium, and for other shielded radioactive sources such as cobalt-60 and cesium-137. In this case, a first parameter extractor 63 is tuned to look for highly attenuating regions in the image where the reconstructed pixel intensity is above a threshold value. This data is passed to the decision tree which seeks to determine whether the attenuating object is part of a larger structure (such as metallic rails which are commonly used to support the framework of a piece of baggage). If the object(s) located by the parameter extractor can not be linked to other structures, the decision tree will evaluate shape, location (for example, is the attenuation object at the surface of the cargo item in which case it may be a fastener) and size prior to passing the new data on to the database search tool. If a match is found between the dark object and a set of characteristics that are common to radioactive sources (typically no re-entrant volume of lower intensity), then an alarm is raised on the operator workstation and the relevant nuclear material is highlighted for inspection. As is commonly known in the art, high density shielding typically has a density of 11 g/cm3 (lead) and above. Standard engineering materials (e.g. steel) tend to have a density of 8 g/cm3 and below. This specific range enables the detection of radioactive source shielding relatively easily.

Points and Knives

In a particular embodiment of the invention, the threat detection processor, which executes programmatic instructions that process input image data 62 and code the decision trees 64 and parameter extractions 63 shown in FIG. 5, is tuned for the detection of sharp objects and knives. Sharp objects are characterized by the presence of a sharp point which is typically distinguished from points that might occur at the non-threatening corners of rectangular objects such as books and electrical goods. Knives are further characterised by the presence of a blade shape which is typically long in one dimension compared to another. In many cases, blades are folded into a supporting housing, and, in this case, the blade is characterized by a repeating structure of high density (case or blade) and low density (surrounding air). A first parameter extractor is tuned for the detection of protruding points and not simply corners. A second parameter extractor is tuned for the detection of blades in which there is a significant length to width aspect ratio. A third parameter extractor is tuned for the detection of folded blades in which there is a repeating structure of at least two air gaps and three material fills.

For example, a three inch blade generally has an aspect ratio (length:width) of at least 3:1 while a six inch blade that of at least 6:1. The width of a blade is generally in proportion to its length, with a width to length ratio on the order of 1:60, and typically less than 1:100 but more than 1:20. Data from these parameter extractors is passed to a decision tree which correlates the data with associated information such as the presence of a handle on a knife.

The filtered information is then passed to a database searcher which analyses the data against known threat items. If a reasonable match is determined, an alarm is raised on the operator workstation and the relevant point or blade is highlighted for further inspection.

Fire-Arms

In a particular embodiment of the invention, the threat detection processor, which executes programmatic instructions that process input image data 62 and code the decision trees 64 and parameter extractions 63 shown in FIG. 5, is tuned for the detection of fire-arms, including gun barrels, steel tubes of a certain diameter (or range of diameters), rifles; and ammunition (a high density slug such as lead, copper, tungsten) next to and connected to a brass cylinder loaded with powder of a known range of densities.

Fire-arms are characterized by the presence of metallic tubes of a certain diameter. Accordingly, a first parameter extractor is tuned for the detection of cylindrical metal tubes. A second parameter extractor is tuned for detection of a trigger mechanism and firing pin. A third parameter extractor is tuned for detection of high density slugs and bullets with composition ranging from aluminium (density 2.7 g/cm3) to lead (density>11 g/cm3). Generally, bullets will have a lower density core filled with gun powder (density typically 1 g/cm3).

Data from these parameter extractors is passed to a decision tree which correlates the data with associated information such as the presence of a gun barrel. The filtered information is then passed to a database searcher which analyses the data against known threat items. If a reasonable match is determined, an alarm is raised on the operator workstation and the relevant cylinder is highlighted for further inspection.

I claim:

1. An X-ray scanning system comprising:
    an X-ray scanner configured to generate scanning data defining a tomographic X-ray image of an object, wherein the X-ray scanner comprises an imaging volume and a plurality of X-ray sources, positioned at least partially around the imaging volume, from which X-rays are directed through the imaging volume, and wherein the X-ray scanner is configured to mimic a rotational motion of the plurality of X-ray sources without physically moving each of the plurality of X-ray sources; and
    at least one processor configured to analyze the scanning data to determine at least one parameter of the tomographic X-ray image and to determine if the object comprises a detonator.

2. The X-ray scanning system of claim 1, wherein the at least one processor is configured to allocate the object to one of a plurality of categories based on the at least one parameter.

3. The X-ray scanning system of claim 1, further comprising a memory storing a plurality of programmatic instructions, wherein the programmatic instructions comprise at least one parameter extractor that, when executed by the at least one processor, is configured to identify at least one predefined feature in the tomographic X-ray image and wherein the predefined feature comprises a plurality of first level parameters of the tomographic X-ray image.

4. The X-ray scanning system of claim 3, wherein the programmatic instructions comprise at least one decision tree for constructing second level parameters based upon the X-ray image.

5. The X-ray system of claim 4, wherein the second level parameters include at least one of a contiguous volume or a predetermined shape.

6. The X-ray scanning system of claim 4, further comprising a plurality of programmatic instructions defining a search tool configured to map the constructed second level parameters of the X-ray image to predefined data.

7. The X-ray scanning system of claim 6, further comprising an alarm system configured to activate an alarm based on a result of mapping the constructed second level parameters of the X-ray image to predefined data, wherein the alarm is indicative of an object being a potential threat.

8. The X-ray scanning system of claim 3, wherein the at least one parameter extractor is configured to operate on at least one of a 2-dimensional image, a 3-dimensional image, or sinogram image data.

9. An X-ray scanning system comprising:
    an X-ray scanner configured to generate scanning data defining a tomographic X-ray image of an object, wherein the X-ray scanner comprises an imaging volume and a plurality of X-ray sources, positioned at least partially around the imaging volume, from which X-rays are directed through the imaging volume and wherein the X-ray scanner is configured to mimic a rotational motion of the a plurality of X-ray sources without physically moving each of the plurality of X-ray sources; and at least one processor configured to analyze the scanning data to determine at least one parameter of the tomographic X-ray image and to determine if the object comprises a gun.

10. The X-ray scanning system of claim 9, wherein the at least one processor is configured to allocate the object to one of a plurality of categories based on the at least one parameter.

11. The X-ray scanning system of claim 9, further comprising a memory storing a plurality of programmatic instructions, wherein the programmatic instructions comprise at least one parameter extractor that, when executed by the at least one processor, is configured to identify at least one predefined feature in the tomographic X-ray image and wherein the predefined feature comprises a plurality of first level parameters of the tomographic X-ray image.

12. The X-ray scanning system of claim 11, wherein the programmatic instructions comprise at least one decision tree for constructing second level parameters based upon the X-ray image.

13. The X-ray system of claim 12, wherein the second level parameters include at least one of a contiguous volume or a predetermined shape.

14. The X-ray scanning system of claim 12, further comprising a plurality of programmatic instructions defining a search tool for configured to map the constructed second level parameters of the X-ray image to predefined data.

15. The X-ray scanning system of claim 14, further comprising an alarm system configured to activate an alarm based on a result of mapping the constructed second level parameters of the X-ray image to predefined data, wherein the alarm is indicative of an object being a potential threat.

16. The X-ray scanning system of claim 11, wherein the at least one parameter extractor is configured to operate on at least one of a 2-dimensional image, a 3-dimensional image or sinogram image data.

17. An X-ray imaging inspection system configured to generate a three dimensional image of at least one object, comprising:
a plurality of X-ray sources distributed at least partially around an imaging volume, wherein the plurality of X-ray sources are configured to emit X-rays which are directed through the imaging volume and wherein the X-ray imaging inspection system is configured to mimic a rotational motion of the plurality of X-ray sources without physically moving each of the plurality of X-ray sources;
an X-ray detector array extending at least partially around the imaging volume and configured to detect X-rays from the plurality of X-ray sources which have passed through the imaging volume and to produce output signals dependent on the detected X-rays;
a conveyor arranged to convey the at least one object through the imaging volume; and
at least one processor configured to analyze the output signals to generate the three dimensional image and determine if the at least one object comprises a security threat.

18. The X-ray imaging inspection system of claim 17, wherein the plurality of X-ray sources is in a plane perpendicular to the direction of movement of the conveyor.

19. The X-ray imaging inspection system of claim 17, wherein each of the plurality of X-ray sources comprises a suppressor and an emitter adjacent the suppressor.

20. The X-ray imaging inspection system of claim 19, wherein each of the plurality of X-ray sources further comprises grid wires positioned above the suppressor and focusing wires parallel to the grid wires.

21. The X-ray imaging inspection system of claim 20, wherein each focusing wire is aligned with a respective grid wires.

22. The X-ray imaging inspection system of claim 20, further comprising an anode positioned above the grid wires and focusing wires.

23. The X-ray imaging inspection system of claim 20, wherein the grid wires are configured to extract a beam of electrons from an area of the emitter.

24. The X-ray imaging inspection system of claim 17, wherein each of the plurality of X-ray sources comprises an extracted beam of electrons configured to be directed at a point on an anode.

25. The X-ray imaging inspection system of claim 20, wherein each of the grid wires are configured to be selectively activated.

26. The X-ray imaging inspection system of claim 25, further comprising a control unit configured to control electrical potentials applied to each of the grid wires to selectively activate each of the grid wires.

27. The X-ray imaging inspection system of claim 17, wherein each of the plurality of X-ray sources emits X-rays for a respective period wherein the respective periods are arranged in a predetermined order.

28. The X-ray imaging inspection system of claim 17, wherein the X-ray detector array is positioned around the imaging volume such that is axially offset from the plurality of X-ray sources.

29. The X-ray imaging inspection system of claim 17, wherein the X-ray detector array comprises a plurality of individual X-ray detectors configured in a linear pattern or ring pattern.

30. The X-ray imaging inspection system of claim 17, wherein the at least one processor is further configured to multiplex the output signals to filter data, adjust gain, and format the data into a data stream.

31. The X-ray imaging inspection system of claim 17, wherein the at least one processor is further configured to generate projection data as a function of an attenuated X-ray beam intensity for X-ray beams emitted from each of the plurality of X-ray sources.

32. The X-ray imaging inspection system of claim 31, wherein the at least one processor is configured to record the projection data as a sinogram arranged in an array with a pixel number along one axis and a source angle along another axis.

33. The X-ray imaging inspection system of claim 17, wherein the at least one processor is a threat detection processor configured to execute one or more parameter extractors that identify at least one parameter in the three dimensional image.

34. The X-ray imaging inspection system of claim 33, wherein the one or more parameter extractors comprise at least one of a grey level or texture.

35. The X-ray imaging inspection system of claim 33, wherein each of the one or more parameter extractors are executed in parallel.

36. The X-ray imaging inspection system of claim 17, wherein the at least one processor is a threat detection processor configured to execute one or more parameter extractors that identify at least one parameter from the three dimensional image, wherein the at least one parameter is passed to a plurality of decision trees.

37. The X-ray imaging inspection system of claim 36, wherein the plurality of decision trees determine a set of information based on the parameters.

38. The X-ray imaging inspection system of claim 37, wherein the set of information comprises at least one of information regarding whether a volume is contiguous, a ratio of a surface area to the volume of an identified region, or a cross-correlation between a shape of the region and template shapes stored in a memory.

39. The X-ray imaging inspection system of claim 37, further comprising a plurality of programmatic instructions that, when executed by the at least one processor, maps the set of information to one of a plurality of threat probabilities.

40. The X-ray imaging inspection system of claim 17, further comprising plurality of programmatic instructions that, when executed by the at least one processor, produces a control output that automatically sorts the at least one object into one of a plurality of categories, wherein the plurality of categories comprises a clear category and a not clear category.

41. The X-ray imaging inspection system of claim 17, wherein the at least one processor is configured to identify parameters in the three dimensional image and wherein the parameters comprise at least one of a mean intensity of pixels within a region of the three dimensional image, a measure of a variance of pixel intensity within the region, or a skewedness of a distribution of pixel values.

42. The X-ray imaging inspection system of claim 41, wherein a non-skewed distribution is indicative of uniform material within the region and a skewed distribution is indicative of non-uniformities in the region.

43. The X-ray imaging inspection system of claim 17, further comprising a workstation configured to display the three dimensional image on a screen and configured to display different sorting decisions using different colors.

44. The X-ray imaging inspection system of claim 17, wherein a speed of scanning the at least one object using the X-ray source is matched to a velocity of the conveyor.

45. The X-ray imaging inspection system of claim 17, wherein the plurality of X-ray sources are configured to extend in a partial arc over the imaging volume.

46. The X-ray imaging inspection system of claim 17, wherein the X-ray source achieves 240 source rotations per second about the conveyor.

47. The X-ray imaging inspection system of claim 17, wherein the conveyor is configured to operate at a speed of 0.5 m/s.

48. The X-ray imaging inspection system of claim 17, wherein the at least one processor is further configured to maximize a distance of an anode irradiation position, relative to a previous anode irradiation position, in order to minimize an instantaneous thermal load on the anode.

49. The X-ray imaging inspection system of claim 17, wherein the X-ray detector array comprises a plurality of scatter detectors.

50. The X-ray imaging inspection system of claim 49, wherein the at least one processor is configured to acquire output signals from the plurality of scatter detectors and reconstruct the output signals from the plurality of scatter detectors into the three dimensional image.

51. The X-ray imaging inspection system of claim 17, wherein the at least one processor is further configured to execute a threat detection algorithm on the three dimensional image.

52. The X-ray imaging inspection system of claim 49, further comprising a collimator positioned in front of each of the plurality of scatter detectors.

53. The X-ray imaging inspection system of claim 17, wherein the X-ray detector array includes a plurality of detectors comprising at least one of GaAs, HgI, CdZnTe or CdTe.

54. The X-ray imaging inspection system of claim 17, wherein the at least one processor is configured to determine a position of a scattering along an X-ray beam direction by a scattered X-ray by identifying an active X-ray source of the plurality of X-ray sources and an axial position of a detector which detects the scattered X-ray.

55. The X-ray imaging inspection system of claim 17, wherein the X-ray detector array comprises a first set of detectors and a second set of detectors and wherein the first set of detectors is positioned at a different axial location along a direction of travel of the conveyor relative to the second set of detectors.

56. The X-ray imaging inspection system of claim 17, wherein the X-ray detector array comprises a first set of detectors and a second set of detectors, wherein the first set of detectors is configured to detect X-rays over a first energy range, wherein the second set of detectors is configured to detect X-rays over a second energy range, and wherein the second energy range is different than the first energy range.

57. The X-ray imaging inspection system of claim 56, wherein the at least one processor is configured to form two sets of image data using the first energy range and the second energy range.

58. The X-ray imaging inspection system of claim 57, wherein the at least one processor is configured to combine the two sets of image data.

59. The X-ray imaging inspection system of claim 56, wherein the at least one processor is configured to record, for each pixel of an image, data for the first energy range and data for the second energy range.

60. The X-ray imaging inspection system of claim 17, wherein the X-ray detector array comprises a first set of detectors and a second set of detectors, wherein the first set of detectors does not comprise a filter, and wherein the second set of detectors comprises a filter.

61. The X-ray imaging inspection system of claim 56, wherein the at least one processor is configured to acquire output signals from the first set of detectors and the second set of detectors and reconstruct the output signals from the first set of detectors and the second set of detectors into the three dimensional image.

62. The X-ray imaging inspection system of claim 17, wherein the at least one processor is further configured to execute a threat detection algorithm on the three dimensional image and wherein the X-ray detector array includes a plurality of detectors comprising at least one of CdZnTe or CdTe.

63. The X-ray imaging inspection system of claim 17, wherein the X-ray detector array comprises a first set of detectors and a second set of detectors, wherein the first set of detectors is sensitive to X-rays of a first energy range, wherein the second set of detectors is sensitive to X-rays of a second energy range, wherein the first energy range is different from the second energy range, wherein the at least one processor is configured to generate the three dimensional image from data generated by the first set of detectors and data generated by the second set of detectors, and wherein the at least one processor is configured to generate a projection image from data generated by the first set of detectors and data generated by the second set of detectors.

64. The X-ray imaging inspection system of claim 17, wherein the X-ray detector array comprises a first set of detectors and a second set of detectors, wherein the first set of detectors is configured to generate data to produce a tomographic image, wherein the second set of detectors is configured to produce a projection image.

65. The X-ray imaging inspection system of claim 64, wherein the projection image is a dual energy projection image.

66. The X-ray imaging inspection system of claim 64, wherein the second set of detectors comprise stacked detectors, wherein detectors on a top side are arranged to detect lower energy X-rays and are transparent to higher energy X-rays, and wherein detectors on a bottom side are arranged to detect the higher energy X-rays.

67. The X-ray imaging inspection system of claim 64, wherein the security threat comprises at least one of a gun or a detonator.

68. An X-ray imaging inspection system configured to generate a three dimensional image of at least one object, comprising:
 a plurality of X-ray sources extending at least partially around an imaging volume, wherein the plurality of X-ray sources are configured to emit and direct X-rays through the imaging volume and wherein the X-ray imaging inspection system is configured to mimic a rotational motion of the plurality of X-ray sources without physically moving each of the plurality of X-ray sources;
 an X-ray detector array extending at least partially around the imaging volume and configured to detect X-rays from the plurality of X-ray sources which have passed through the imaging volume and to produce output signals dependent on the detected X-rays, wherein the X-ray detector array includes a plurality of detectors comprising at least one of GaAs, HgI, CdZnTe or CdTe;
 a conveyor arranged to convey the at least one object through the imaging volume; and
 at least one processor configured to analyze the output signals to generate the three dimensional image and identify if the at least one object comprises a security threat; and
 a plurality of programmatic instructions that, when executed by the at least one processor, produces a control output that automatically sorts the at least one object into one of a plurality of categories, wherein the plurality of categories comprises a clear category and a not clear category.

69. The X-ray imaging inspection system of claim 68, wherein the at least one processor is configured to form two sets of image data using data having a first energy range and data having a second energy range generated from the plurality of detectors.

70. The X-ray imaging inspection system of claim 69, wherein the at least one processor is configured to combine the two sets of image data.

71. The X-ray imaging inspection system of claim 69, wherein the at least one processor is configured to record, for each pixel of an image, data for the first energy range and data for the second energy range.

72. The X-ray imaging inspection system of claim 68, wherein the at least one processor is further configured to execute a threat detection algorithm on the three dimensional image.

73. The X-ray imaging inspection system of claim 68, wherein the plurality of detectors comprise a first set of detectors and a second set of detectors and wherein the first set of detectors is positioned at a different axial location along a direction of travel of the conveyor relative to the second set of detectors.

74. The X-ray imaging inspection system of claim 68, wherein the plurality of X-ray sources are configured to extend in a partial arc over the imaging volume.

75. The X-ray imaging inspection system of claim 68, wherein the conveyor is configured to operate at a speed of 0.5 m/s.

76. The X-ray imaging inspection system of claim 68, further comprising a workstation configured to display the three dimensional image on a screen and configured to display different sorting decisions using different colors.

77. The X-ray imaging inspection system of claim 68, wherein the at least one processor is a threat detection processor configured to execute one or more parameter extractor that identify at least one parameter in the three dimensional image.

78. The X-ray imaging inspection system of claim 68, wherein the X-ray detector array is positioned at least partially around the imaging volume such that is axially offset from the plurality of X-ray sources.

79. The X-ray imaging inspection system of claim 68, wherein each of the plurality of X-ray sources comprises an extracted beam of electrons configured to be directed at a point on an anode.

80. The X-ray imaging inspection system of claim 68, wherein the security threat comprises at least one of a gun or a detonator.

* * * * *